US010088663B2

(12) United States Patent
Ozcan et al.

(10) Patent No.: US 10,088,663 B2
(45) Date of Patent: Oct. 2, 2018

(54) DEVICE AND METHOD FOR TUNABLE VAPOR CONDENSED NANOLENSES

(71) Applicant: THE REGENTS OF THE UNIVERSITY OF CALIFORNIA, Oakland, CA (US)

(72) Inventors: Aydogan Ozcan, Los Angeles, CA (US); Euan McLeod, Alhambra, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 189 days.

(21) Appl. No.: 15/154,279

(22) Filed: May 13, 2016

(65) Prior Publication Data
US 2016/0334614 A1 Nov. 17, 2016

Related U.S. Application Data

(60) Provisional application No. 62/161,176, filed on May 13, 2015.

(51) Int. Cl.
G02B 21/36 (2006.01)
G03H 1/04 (2006.01)
(Continued)

(52) U.S. Cl.
CPC ............ *G02B 21/365* (2013.01); *B05D 1/60* (2013.01); *C23C 14/12* (2013.01); *C23C 14/223* (2013.01);
(Continued)

(58) Field of Classification Search
None
See application file for complete search history.

(56) References Cited

U.S. PATENT DOCUMENTS

2006/0257662 A1* 11/2006 Bujard ................. C09C 1/0015
428/404
2010/0232161 A1* 9/2010 Aschwanden ........... G02B 3/14
362/278
(Continued)

FOREIGN PATENT DOCUMENTS

| WO | 2013/019640 A1 | 2/2013 |
| WO | 2013/184835 A1 | 12/2013 |
| WO | 2013/184835 A9 | 12/2013 |

OTHER PUBLICATIONS

Lee, T.D. Surface Characterization by Heterogeneous Nucleation from the Vapor. (1998).
(Continued)

Primary Examiner — Eileen M Adams
(74) Attorney, Agent, or Firm — Vista IP Law Group LLP

(57) ABSTRACT

A method of forming nanolenses for imaging includes providing an optically transparent substrate having a plurality of particles disposed on one side thereof. The optically transparent substrate is located within a chamber containing therein a reservoir holding a liquid solution. The liquid solution is heated to form a vapor within the chamber, wherein the vapor condenses on the substrate to form nanolenses around the plurality of particles. The particles are then imaged using an imaging device. The imaging device may be located in the same device that contains the reservoir or a separate imaging device.

17 Claims, 12 Drawing Sheets

(51) Int. Cl.
| | |
|---|---|
| B05D 1/00 | (2006.01) |
| C23C 14/12 | (2006.01) |
| C23C 14/22 | (2006.01) |
| C23C 14/54 | (2006.01) |
| G01N 15/14 | (2006.01) |
| B82Y 20/00 | (2011.01) |

(52) U.S. Cl.
CPC ....... *C23C 14/541* (2013.01); *G01N 15/1468* (2013.01); *G02B 21/361* (2013.01); *G03H 1/0443* (2013.01); *B82Y 20/00* (2013.01); *G03H 2001/046* (2013.01); *G03H 2001/0447* (2013.01); *G03H 2001/0452* (2013.01); *G03H 2222/34* (2013.01); *G03H 2240/56* (2013.01); *Y10S 977/881* (2013.01); *Y10S 977/891* (2013.01)

(56) References Cited

U.S. PATENT DOCUMENTS

| | | | |
|---|---|---|---|
| 2010/0303692 A1* | 12/2010 | Perkins | C01B 3/22 422/639 |
| 2011/0092007 A1* | 4/2011 | Lee | G02B 5/1857 438/32 |
| 2012/0314185 A1* | 12/2012 | Bauman | G02B 1/043 351/159.33 |
| 2013/0258091 A1 | 10/2013 | Ozcan et al. | |
| 2016/0089677 A1* | 3/2016 | Cheng | B03C 1/031 209/214 |

OTHER PUBLICATIONS

Allier, C.P. et al., Thin welling film lensless imaging, Proc. of SPIE, 7906, 760608-1-760608-8 (2011).
Allier, C.P. et al., Bacteria detection with thin wetting film lensless imaging, Biomedical Optics Express, 1(3):762-770 (2010).
Bishara, Waheb et al., Holographic pixel super-resolution in portable lensless on-chip microscopy using a fiber-optic array, Lab Chip, Apr. 7, 2011; 11(7):1276-1279.
Bishara, Waheb et al., Lensfree on-chip microscopy over a wide field-of-view using pixel super-resolution, Opt Express, May 24, 2010; 18(11), 11181-11191.
Hennequin, Yves et al., Optical Detection and Sizing of Single Nano-Particles Using Continuous Wetting Films, ACS Nano., Sep. 24, 2013; 7(9): 7601-7609.
Hofer, R. et al., Imaging of Surface Heterogeneity by the Microdroplet Condensation Technique, Langmuir 2001, 17, 4123-4125.
Gorocs, Zoltan et al., On-Chip Biomedical Imaging, IEEE Rev in Biomed Eng., 6:29-46 (2013).
Isikman, Serhan et al., Lensfree Cell Holography on a Chip: From Holographic Cell Signatures to Microscopic Reconstruction, Proceedings of IEEE Photonics Society Annual Fall Meeting, pp. 404-405 (2009).
Lopez, Gabriel et al., Imaging of Features on Surfaces by Condensation Figures, Science, 260, 647-649 (1993).
Mudanyali, Onur et al., Compact, light-weight and cost-effective microscope based on lensless incoherent holography for telemedicine applications, Lab Chip, 2010, 10, 1417-1428.
Mudanyali, Onur et al., Wide-field optical detection of nanoparticles using on-chip microscopy and self-assembled nanolenses, Nature Photonics, 7, 247-254 (2013).
Oh, Chulwoo et al., On-chip differential interference contrast microscopy using lensless digital holography, Opt Express, 18(5):4717-4726 (2010).

* cited by examiner

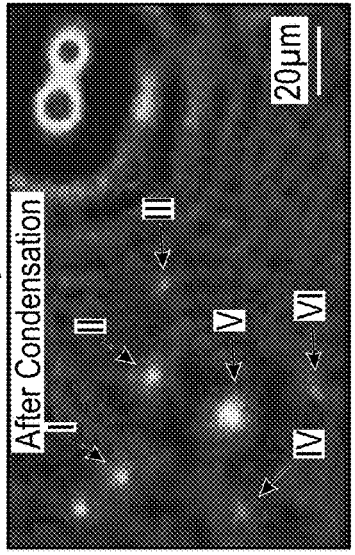
FIG. 4I
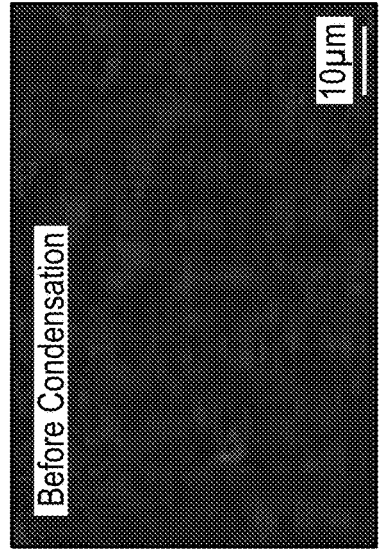
FIG. 4J
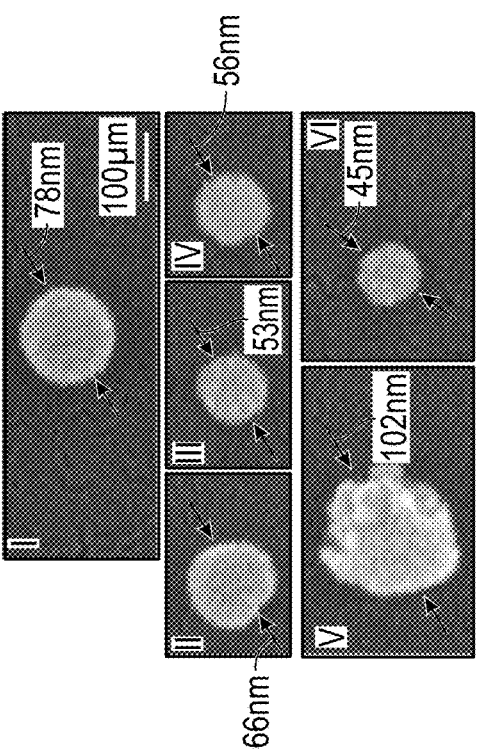
FIG. 4K
FIG. 4L

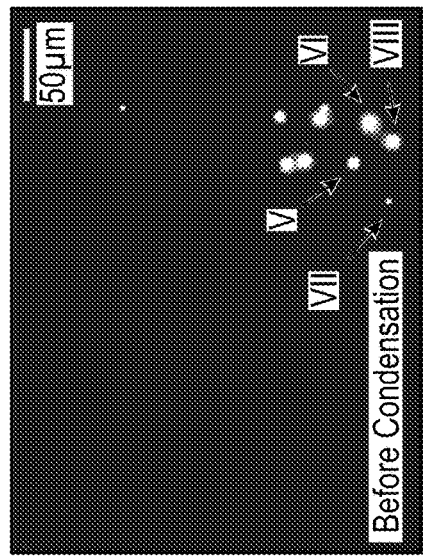
FIG. 5F Before Condensation
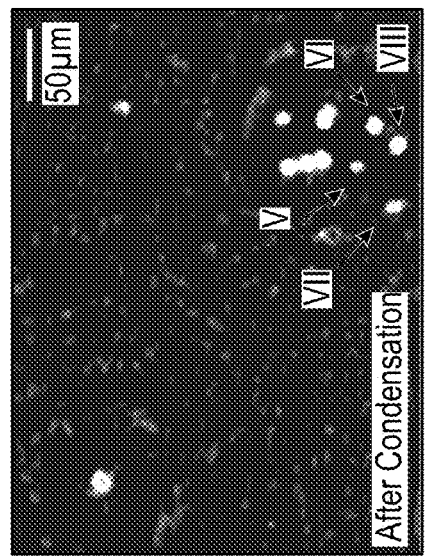
FIG. 5H After Condensation
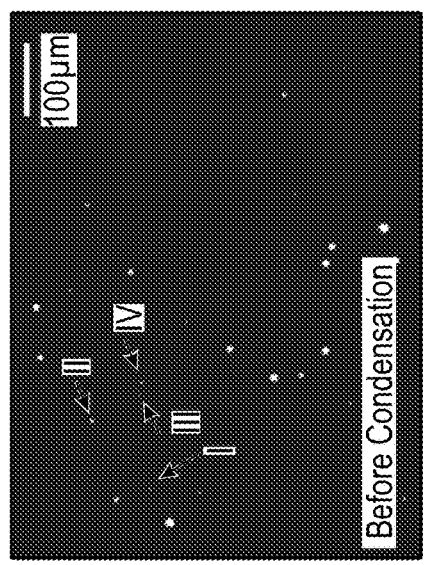
FIG. 5E Before Condensation
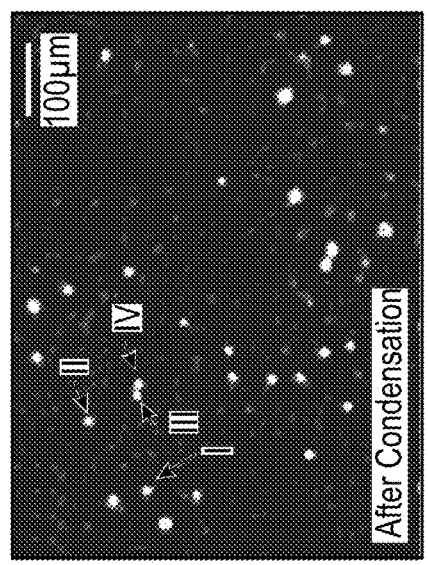
FIG. 5G After Condensation

DEVICE AND METHOD FOR TUNABLE VAPOR CONDENSED NANOLENSES

RELATED APPLICATION

This application claims priority to U.S. Provisional Patent Application No. 62/161,176 filed on May 13, 2015, which is hereby incorporated by reference in its entirety. Priority is claimed pursuant to 35 U.S.C. § 119.

STATEMENT REGARDING FEDERALLY SPONSORED RESEARCH AND DEVELOPMENT

This invention was made with Government support under W911NF-13-1-0419, awarded by the U.S. Army, Army Research Office. The Government has certain rights in the invention.

TECHNICAL FIELD

The technical field generally relates to imaging methods and more specifically to nano-structured optical components such as nanolenses to control light at sub-wavelength scales.

BACKGROUND

Digital holography has been experiencing a rapid growth over the last several years, together with the availability of cheaper and better digital components as well as more robust and faster reconstruction algorithms, to provide new microscopy modalities that improve various aspects of conventional optical microscopes. In an effort to achieve wide-field on-chip microscopy, the use of unit fringe magnification (F~1) in lens-free in-line digital holography to claim an FOV of ~24 mm² with a spatial resolution of <2 µm and an NA of ~0.1-0.2 has been demonstrated. See Oh C. et al., On-chip differential interference contrast microscopy using lens-less digital holography, Opt Express.; 18(5):4717-4726 (2010) and Isikman et al., Lens-free Cell Holography On a Chip: From Holographic Cell Signatures to Microscopic Reconstruction, Proceedings of IEEE Photonics Society Annual Fall Meeting, pp. 404-405 (2009). This work used a spatially incoherent light source that is filtered by an unusually large aperture (~50-100 µm diameter); and unlike most other lens-less in-line holography approaches, the sample plane was placed much closer to the detector chip rather than the aperture plane, i.e., $z_1 \gg z_2$. This unique hologram recording geometry enables the entire active area of the sensor to act as the imaging FOV of the holographic microscope since F~1.

More recently, a lens-free super-resolution holographic microscope has been proposed which achieves sub-micron spatial resolution over a large field-of-view of e.g., ~24 mm². See Bishara et al., "Holographic pixel super-resolution in portable lensless on-chip microscopy using a fiber-optic array," Lab Chip 11, 1276 (2011). The microscope works based on partially-coherent lens-free digital in-line holography using multiple light sources (e.g., light-emitting diodes—LEDs) placed at ~3-6 cm away from the sample plane such that at a given time only a single source illuminates the objects, projecting in-line holograms of the objects onto a CMOS sensor-chip. Because the objects are placed very close to the sensor chip (e.g., ~1-2 mm) the entire active area of the sensor becomes the imaging field-of-view, and the fringe-magnification is unit. As a result of this, these holographic diffraction signatures are unfortunately under-sampled due to the limited pixel size at the CMOS chip (e.g., ~2-3 µm). To mitigate this pixel size limitation on spatial resolution, several lens-free holograms of the same static scene are recorded as different LEDs are turned on and off, which creates sub-pixel shifted holograms of the specimens. By using pixel super-resolution techniques, these sub-pixel shifted under-sampled holograms can be digitally put together to synthesize a smaller effective pixel size of e.g., ~300-400 nm, which can now resolve/sample much larger portion of the higher spatial frequency oscillations within the lens-free object hologram. Unfortunately, the imaging performance of this lens-free microscopy tool is still limited by the detection SNR, which may pose certain limitations for imaging of e.g., weakly scattering phase objects that are refractive index matched to their surrounding medium such as sub-micron sized bacteria in water.

One approach to imaging small particles using lens-free holographic methods such as those disclosed above include the use of smaller pixel sizes at the sampling (i.e., detector plane). However, such a sampling related bandwidth increase only translates into better resolution if the detection SNR is maintained or improved as the pixel size of the imager chip is reduced. Therefore, the optical design of the pixel architecture (especially in CMOS imager technology) is extremely important to maintain the external quantum efficiency of each pixel over a large angular range. While reduced pixel sizes (e.g. <1 µm) and higher external quantum efficiencies can further improve the resolution of lens-free on-chip microscopy to, e.g., the sub-200 nm range in the future, other sample-preparation approaches have been attempted to improve SNR.

Wetting thin-film dynamics have been studied in chemistry and biology and attempts have been made to incorporate the same in imaging modalities. Among these prior results, a recent application of thin wetting films towards on-chip detection of bacteria provides an approach where the formation of evaporation-based wetting films was used to enhance e.g., diffraction signatures of bacteria on a chip. See e.g., C. P. Allier et al., Thin wetting film lensless imaging, Proc. SPIE 7906, 760608 (2011). PCT Publication No. WO 2013/019640 discloses a holographic microscopic method that uses wetting films to image objects. In that method a droplet is mechanically vibrated to create a thin wetting film that improves imaging performance. PCT Publication No. WO 2013/184835 discloses a method whereby the substrate is tilted to gravitationally drive a droplet to an edge of the substrate while forming a dispersed monolayer of particles having liquid lenses surrounding the particles. Other attempts have been made to form lenses around microparticles using the evaporation of water from aqueous suspensions containing a dissolved polymer. For example, Hennequin et al., Optical Detection and Sizing of Single Nanoparticles Using Continuous Wetting Films, ACS Nano, 7 (9), pp. 7601-7609 (2013) discloses such a method for the detection and sizing of 100-200 nm particles. Still further improvements are needed to image small, nano-scale particles such as viruses and the like and in particular objects smaller than 100 nm.

SUMMARY

According to one embodiment, a method of forming nanolenses for imaging includes providing an optically transparent substrate having a plurality of particles disposed on one side thereof. The optically transparent substrate is located or placed within a chamber containing therein a reservoir holding a liquid solution. The liquid solution is heated to form a vapor within the chamber, wherein the vapor condenses on the substrate to form nanolenses around the plurality of particles. The particles with the nanolenses formed thereon can then be imaged with an imaging device. In one aspect, the imaging device is incorporated into the same device used for vapor generation and condensation. In another aspect of the invention, a separate imaging device is used where the substrate is removed and transferred from the nanolens-forming device and imaged in a separate imaging device (e.g., lens-free or lens-based imaging device). The liquid may include a number of different fluids but in one particular preferred embodiment, the liquid is a polymer and in particular polyethylene glycol (PEG).

In another embodiment of the invention, a method of imaging particles includes providing an optically transparent substrate having the particles disposed on one side thereof and heating a liquid solution contained in a reservoir to generate vapor that is exposed to the optically transparent substrate, wherein the vapor condenses on the substrate to form nanolenses around the particles. The particles with the nanolenses are then imaged with an imaging device.

In another embodiment, a method of forming nanolenses for imaging includes the steps of providing a chilled, optically transparent substrate having a plurality of particles disposed on one side thereof. This chilled substrate is then exposed to a vapor that condenses on the chilled substrate to form self-assembled nanolenses around the plurality of particles. The vapor may be present in the ambient environment (e.g., water vapor) or, alternatively, the chilled substrate may be located in an enclosed chamber or environment that contains a reservoir with fluid contained therein. Such a fluid reservoir does not necessarily need to be heated.

In another embodiment, the invention pertains to a device platform or system that enables the tunable formation of nanolenses via condensation of a heated liquid around nanometer-sized particles contained on an optically transparent substrate. The liquid may include, for example, liquid polyethylene glycol (PEG) that is heated to form a vapor that then condenses on the substrate around the particles to form nanolenses. In one embodiment, a device for forming nanolenses includes a closed housing or chamber that includes a reservoir configured to hold a liquid such as the polyethylene glycol (PEG). A heating element is in thermal contact with the reservoir (or contents of the reservoir) and is used to heat the liquid. An optically transparent substrate having opposing surfaces and containing a plurality of particles on one of the surfaces is disposed adjacent to or near the reservoir such that the surface of the substrate containing the particles faces the reservoir. The reservoir and substrate may both be contained within a common chamber or housing is used to contain liquid vapor. The device includes a light source or multiple light sources that is/are configured to illuminate the substrate and an image sensor disposed adjacent to the substrate. Holographic images of the particles are acquired using the image sensor. Raw holographic images can be processed by a separate processor or multiple processors (e.g., a computing device) to produce a super-resolved, reconstructed image of the particles. The heating element is used to heat the liquid to form a vapor that condenses on the substrate around the particles to form nanolenses.

Previous nanoparticle imaging efforts across similar FOVs have detected spheroids no smaller than 100 nm. The results demonstrated herein disclose the detection of particles with more than 15-fold smaller volumes, which in free space have >240 times weaker Rayleigh scattering compared to the particle sizes detected in earlier wide-field imaging work. This entire platform, with its tunable nanolens condensation and wide-field imaging functions, is also miniaturized, in one embodiment, into a cost-effective and portable device, which might be especially important for field use, mobile sensing, and diagnostics applications, including e.g., the measurement of viral loads in bodily fluids. In addition to its tunability and significant SNR improvement in wide-field nano-object imaging, this vapor-condensation approach to nanolens fabrication can be used in many other applications, ranging from emissivity enhancement and improved collection efficiency to sub-diffraction-limit resolution.

While other methods exist for detecting nanoparticles, vapor-condensed nanolenses improve the detection SNR by more than a factor of 50 and enable the detection of particularly small particles including spheres <40 nm and rods <20 nm in diameter across an ultra-large FOV of 20 $mm^2$, i.e., >1,000 fold larger compared to the FOV of e.g., a 100× objective-lens. These vapor-condensed nanolenses are also compatible with chemically functionalized surfaces for specific and sensitive capture and detection of bioparticles such as viruses.

The system and methods described herein may be applicable to image a wide range of particles and objects. These include both organic and inorganic particles. For example, in one particular embodiment, environmental particles (e.g., waterborne or airborne particulates) are imaged using nanolenses. The nanolenses can also be used to image biological particles.

BRIEF DESCRIPTION OF THE DRAWINGS

FIG. 4I illustrates another holographic image of a region of interest containing gold nanoparticles before condensation.

FIG. 4J illustrates another holographic image of a region of interest containing gold nanoparticles after condensation. In addition to the nanoparticles, this region of interest includes two very large dust particles, which can be seen in both the 'before' image FIG. 4I and the 'after' image of FIG. 4J, showing that the two images are correctly registered.

FIG. 4K illustrates SEM images of the gold nanoparticles of FIG. 4J. Measured dimensions are also illustrated.

FIG. 4L illustrates another holographic image of a region of interest containing large, multi-walled carbon nanotubes before condensation.

FIGS. 5E and 5F illustrates conventional fluorescent 40× objective microscope images showing specific capture of only streptavidin-coated beads.

FIG. 5G illustrates holographic images of the sample of FIG. 5E with vapor-condensed nanolenses showing particle detection.

FIG. 5H illustrates holographic images of the sample of FIG. 5F with vapor-condensed nanolenses showing particle detection.

DETAILED DESCRIPTION OF ILLUSTRATED EMBODIMENTS

Figure 1A:
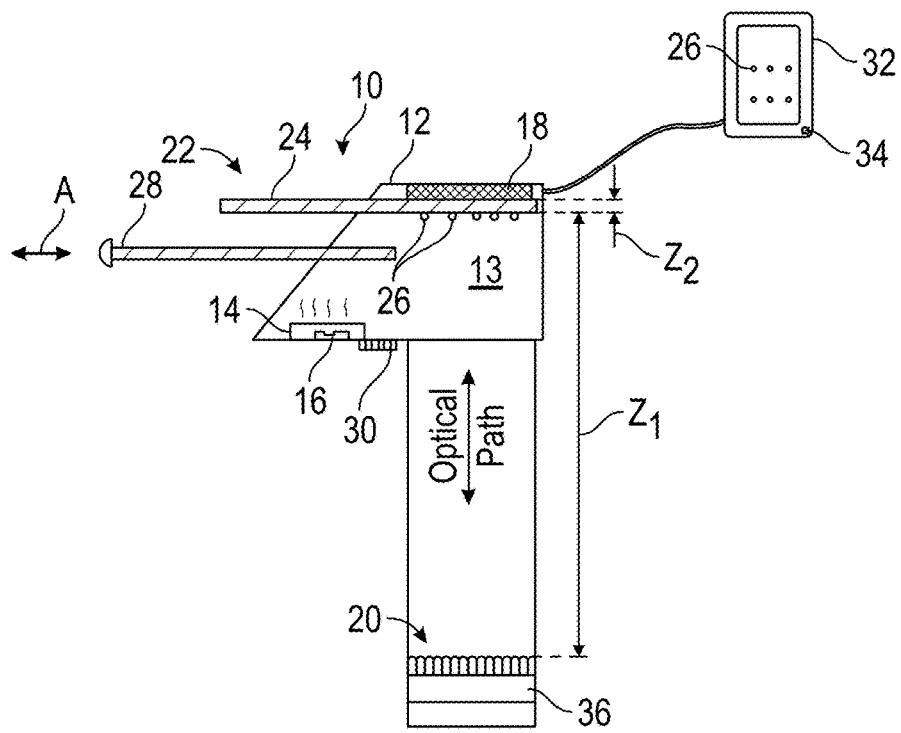
FIG. 1A illustrates schematically one embodiment of a device for forming nanolenses around particles.

FIG. 1A illustrates a device 10 for forming nanolenses according to one embodiment. The device 10 includes a housing 12 that holds the various components of the device 10. The housing 12 may be made from a polymer material in order to make the device 10 lightweight although other materials may also be used. The housing 10 defines an interior chamber 13 that contains various components of the device 10. In one embodiment, housing 10 is substantially sealed so that, as explained herein, vapor that is generated within the chamber 13 remains inside. Alternatively, in another alternative embodiment, the housing 10 may be open to the external environment such that some vapor may exit the interior chamber 13.

With reference to FIG. 1A, a reservoir 14 is provided inside the chamber 13 within the housing 10 that is dimensioned to hold a liquid. The reservoir 14 may include a recess, chamber, or other structure that is capable of retaining a fluid therein. For example, the reservoir 14 may include a container, cup, or receptacle that is defined by one or more walls and includes an open or exposed end (e.g., top end) so that when heated vapor is able to form and move within the interior chamber 13. In one aspect of the invention, the liquid that is contained in the reservoir 14 is polyethylene glycol (PEG) although other liquids such as glycerol, water, or silicone oil may also be used. The reservoir 14 contains a heating element 16 that is in thermal contact with the reservoir 14 and/or the fluid that is contained within the reservoir 14. The heating element 16 may include a resistive heater that generates heat in response to current flowing through the same. Power to the resistive heater may be provided by one or more batteries (not shown) that are stored in the device 10 or the resistive heater may be powered by an external power source (e.g., a wall socket that the device 10 plugs into). The heating element 16 may be coupled to a temperature sensor such as a thermistor or the like that is used to control the temperature of the liquid contained in the reservoir 14. Control circuitry (e.g., temperature controller 30) provided in the device 10 may be used to receive a signal from the temperature sensor and adjust the heating element 16 (e.g., turn on/off or adjust duty cycle) so that the temperature of the liquid can be controlled. As explained herein, the liquid contained in the reservoir 14 is heated to generate a vapor that enters the interior chamber 13 and then condenses on a sample holder (e.g., substrate) that contains the small sized objects or particles to form "nanolenses." The temperature to which the liquid is heated may vary depending on the type of fluid that is used but generally is within the range of 50° C. to 250° C.

The device 10 includes an image sensor 18 disposed in or on the housing 12 and is situated opposite to a light source 20. The image sensor 18 may include a CMOS image sensor or the like. The light source 20, in one preferred embodiment, may include a plurality of spatially separate light sources. For example, the light source 20 may include a linear array of LEDs or the like that can be selectively activated. In this example, the linear array of twenty (20) LEDs is oriented at a diagonal with respect to image sensor 18. The diagonal orientation allows multiple images to be taken with x and y offsets so that a pixel super-resolution hologram can be generated. Each individual LED within the diagonal array generates a different x-direction and y-direction offset. These different images can then be digitally merged to create a pixel super-resolution hologram that has an effective pixel size that is smaller than the physical pixel size of the image sensor 18. The device 10 illuminates the sample from the different spatial locations which are then combined to create a higher resolution image. Details of the pixel super-resolution process may be found in PCT Patent Application No. PCT/US2016/14560, U.S. Patent Application Publication No. 2013-0258091, Bishara et al., Lensfree on-Chip Microscopy over a Wide Field-of-View Using Pixel Super-Resolution, Opt. Express, 18, 11181-11191 (2010), and Bishara et al., "Holographic pixel super-resolution in portable lensless on-chip microscopy using a fiber-optic array," Lab Chip 11, 1276 (2011), all of which are incorporated herein by reference.

The housing 12 is configured to hold a sample holder 22 that, in one embodiment, includes an optically transparent substrate 24 such as plasma-treated glass (to render the same hydrophilic). A sample that contains particles or objects 26 (e.g., nanometer-sized particles although the particles 26 may be larger) is then placed on the substrate 24. Particles 26 may include organic or inorganic matter. Particles 26 may include small particulate matter that is found in the environment. For example, particulate matter is a known air pollutant that is often monitored by environmental health authorities. In one embodiment, the particles 26 may include particulate matter that is airborne and captured onto the substrate 24. For example, the sample substrate 24 may be exposed to air for a period of time whereby particles 26 accumulate on the surface of the substrate 24. These samples may then be subject to nanolens formation as described herein and imaged. In another embodiment, the particles 26 may include particulate matter that is waterborne and captured on an optically transparent substrate 24. The particles 26 may also include biological-based particles. Examples of biological based particles 26 include, without limitation, biomolecules, viruses, bacteria, prions, cells, and cellular components or constituents.

Typically, the sample is a fluid solution that contains particles 26 therein that is deposited onto the surface of the substrate 24. The fluid is allowed to evaporate leaving the particles 26 behind on the substrate 24. However, as explained above, in other embodiments, a fluid solution is not used to deposit the particles 26 and the substrate 24 is used to directly acquire the particles 26 (e.g., the substrate 24 may be exposed to the air directly). The particles 26 may be randomly distributed on the surface of the substrate 24 or, alternatively, they may be patterned in an array or the like (e.g., using a patterned biding agent on the substrate 24). The particles 26 may adhere to the substrate 24 through Van der Waals attractive force or through intermediary such as molecule or chemical moiety (e.g., a binding agent) that is affixed to the substrate 24 and selectively binds particles 24. The substrate 24 may, optionally, have an electrical charge (e.g., electrostatic charge) that aids in capturing particles 26.

The use of a binding agent may be used when the device 10 is operated to detect the presence of a particular particle 26 or object type. For example, if the device 10 were to be used for virus detection, a binding agent that is specific to the target virus may adhered to the substrate 24. A sample can then be placed on the substrate 24 (or exposed to the substrate 24) and allowed to incubate for a period of time. If virus is present in the sample, it will bind or adhere to the binding agent and is then detected using the imaging functionality described herein. Note that different types of binding agents may be used on a single substrate 24 so that multiplexed detection may take place. The location of a particular binding agent is known in advance and can be used to determine the presence or absence of a target analyte or species within a sample depending on whether binding occurs or not at the particular site of interest.

The sample holder 22 can preferably be inserted into the housing 12 of the device 10 (as well as removed from the housing 12). When fully inserted into the housing 12, the side of the substrate 24 that contains the particles 26 is facing toward the reservoir 14 (e.g., in this case facing down toward reservoir 14). In this embodiment, the reservoir 14 is laterally disposed somewhat relative to the substrate 24 so that the reservoir 14 does not block the optical path formed between the substrate 24 and the light source 20. An optional shutter 28 may be disposed in the housing 12 that can be moved back and forth in direction of arrow A to limit condensation of vapor onto the substrate 24. For example, the location of the shutter 28 may be such that advancement of the same provides a physical barrier between the reservoir 14 and the substrate 24 such that additional vapor generated from the reservoir 14 will not be able to condense on the substrate 24. The optional shutter 28 may be used to modulate the condensation growth of the liquid around the particles 26. The light source 20 is generally positioned at a much larger distance $z_1$ from the particles 26 as compared to the distance $z_2$ between the particles 26 and the image sensor 18 (i.e., $z_1 \gg z_2$). For example, the distance $z_2$ may be on the order of 1 mm or less while the distance $z_1$ may be on the order of several centimeters.

The temperature of the fluid or liquid contained within the reservoir 14 may be controlled using a computer-controlled temperature controller 30 that may be located outside the housing 12 or, alternatively, integrated therein. The temperature controller 30 may receive temperature data from a temperature sensor such as a thermocouple or the like that is immersed within the reservoir 14. In this regard, the temperature of the fluid (e.g., PEG fluid) can be controlled to be within a certain range. For example, for PEG fluid a temperature within the range of 85° C. to 105° C. may be used. A higher temperature will yield a faster operation but less precision in results. Typically, the fluid is heated to an elevated temperature so that vapor is formed within the interior chamber 13 but not above the boiling point of the fluid. As noted herein, generally the temperature of the heated solution is within the range of 50° C. to 250° C.

Still referring to FIG. 1A, in one embodiment the device 10 is connected to a computing device 32. The computing device 32 may include any number of devices such as personal computer, laptop, tablet, PDA, or mobile communication device (e.g., Smartphone). The computing device 32 includes therein one or more processors 34 therein that are used to execute image acquisition and image processing software for the reconstruction of a high resolution image of the particles 26 based on multiple image frames obtained from the image sensor 18. In an alternative configuration, the functionality of the computing device 32 may be integrated into the device 10 such that the processor 34 can be integrated into or on the housing 12, for example. Likewise, in another alternative embodiment, rather than rely on a separate image sensor 18 an image sensor of the computing device 32 (e.g., mobile phone camera) could be used. In such an alternative embodiment, the housing 12 would merely omit the image sensor and would be positioned on the computing device 32 to align the optical path with the camera of the computing device 32. In such an alternative embodiment, it may be necessary to remove the lens of the computing device 32 that was installed by the manufacturer (or incorporate other compensating lenses).

With reference to FIG. 1A, the interior chamber 13 of the housing 12 containing, for example, the reservoir 14 may largely be isolated or sealed from the external environment. In this configuration, for example, PEG vapor is trapped or otherwise contained within the interior chamber 13 that is substantially sealed from the exterior environment. However, in other embodiments, the housing 12 may be open such that some of the generated vapor may escape to the external environment. The device 10 may also include a door or lid so that vapor contained therein may be selectively allowed to escape (e.g., between measurements).

FIG. 1A also illustrates that the device 10 may include a power source 36 therein. The power source 36 may include batteries, for example, that are used to power the LEDs making up the light source 20, the heating element 16, the image sensor 18, and the temperature controller 30. Alternatively, the device 10 may draw power from the connected computing device 32. As another alternative, the device 10 may be connected to an AC or DC sources of power through a power cord or the like that is commonly used in connection with consumer electronic devices.

To use the device 10, a substrate 24 containing particles 26 thereon is inserted into the housing 12. The reservoir 14 contains a liquid therein or is loaded with a liquid (e.g., PEG). The liquid is then heated with heating element 16. Vapor is then created inside the interior chamber 13 of the housing 12 and condenses on the facing side of the substrate 24 containing the particles 26. The condensation forms nanolenses 40 around each particle 26. The thickness of the condensed liquid increases with time and thus alters the geometry of the nanolenses 40 as a function of time. It is expected that several minutes may be needed to deposit the desired amount of liquid, however, nanolenses 40 may be formed around the particles 26 after several seconds in some instances. During this condensation process, the particles 26 may be concurrently imaged so that the time-wise progression may be monitored. Alternatively, the particles 26 may be imaged at an end point after a certain amount of time has elapsed.

Figure 1B:
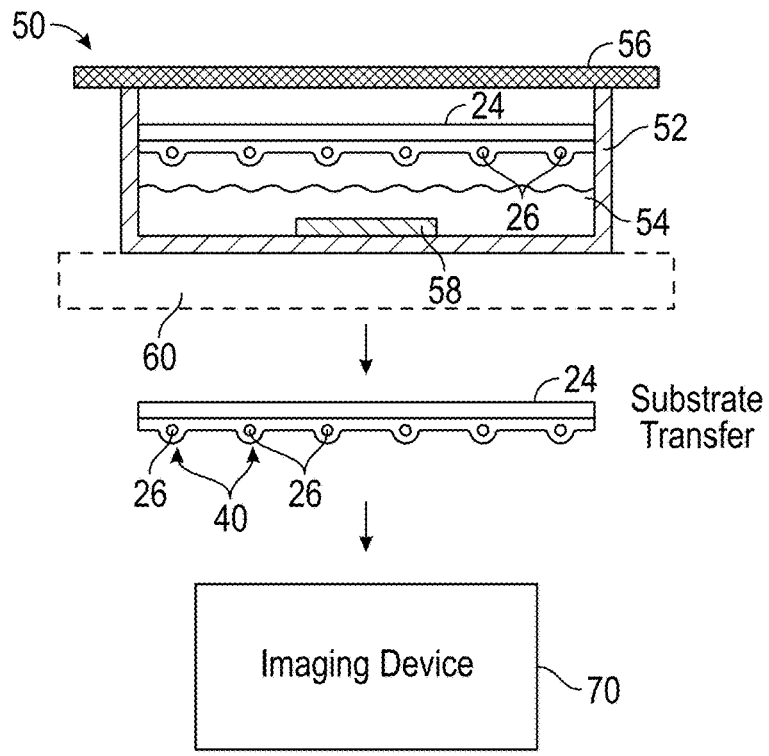
FIG. 1B illustrates schematically another embodiment of a device for forming nanolenses around particles.

FIG. 1B illustrates an alternative system or arrangement that is used to form nanolenses 40. In this embodiment, the substrate 24 (which may be optically transparent) containing the particles 26 on one surface thereof is placed inside a lens-forming device 50. The lens-forming device 50 includes a reservoir 52 that contains a fluid 54 (e.g., PEG or any other liquid contemplated herein). The reservoir 52 may be formed in all or a portion of the base of the device as is illustrated in FIG. 1B. The substrate 24 containing the particles 26 is suspended over the reservoir 52 containing the fluid 54 such that the side of the substrate 24 that contains the particles 26 is facing the fluid 54 as illustrated in FIG. 1B. The substrate 24 may be held over the reservoir 52 using a rack, jig, or mount system such that the face of the substrate 24 that contains the particles 26 is largely fully exposed to the fluid 54. A lid or cap 56 is provided that substantially seals the interior of the lens-forming device 50 so that vapor that is generated therein by heating (as explained below) remains inside the device 50. The cover, lid, or cap 56 is also removable such that after lens formation the substrate 24 can be removed from the device 50 and transferred to an imaging device 70 for imaging.

As seen in FIG. 1B, the lens-forming device 50 may include a heater 58 therein that heats the fluid 54. Power delivered to the heater 58 heats the fluid 54 which then creates fluid vapor that bathes the substrate 24. Alternatively, the lens-forming device 50 may not include a heater 58 and the device 50 or reservoir 52 is placed on a heater such as a hot plate 60 that provides the heat. For example, the lens-forming device 50 may include a dish as the reservoir 52 along with a cover, lid, or cap 56. The entire assembly is placed on a hot plate 60. This is also illustrated, for example, in FIG. 3B. Note that the imaging device 70 may include a number of imaging devices. It may include an imaging device such as the lens-free imaging device illustrated in FIGS. 1A, 3D, and 3E or it may include a lens-free imaging device such as that illustrated in FIG. 3C. In addition, in another alternative embodiment, the imaging device 70 may be a conventional optical microscope or the like. The nanolenses 40 contribute to added resolution even for this imaging modality.

Figure 2:
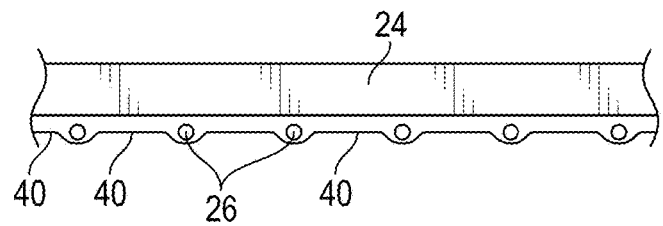
FIG. 2 illustrates a magnified side view of a substrate having particles disposed on a first side thereof and nanolenses formed around the particles using a device of the type of FIG. 1.

FIG. 2 illustrates a magnified view of a substrate 24 having particles 26 disposed thereon with polymer nanolenses 40 formed around each particle 26. The nanolenses 40 are formed by exposing the particles 26 to polymer vapor (e.g., PEG vapor) for a period of time such that the vapor condenses to form lenses 40 around the particles 26. Notice that the lenses 40 are formed as part of a continuous film on the substrate 24 as opposed to being discrete and separate lenses.

Figure 3A:
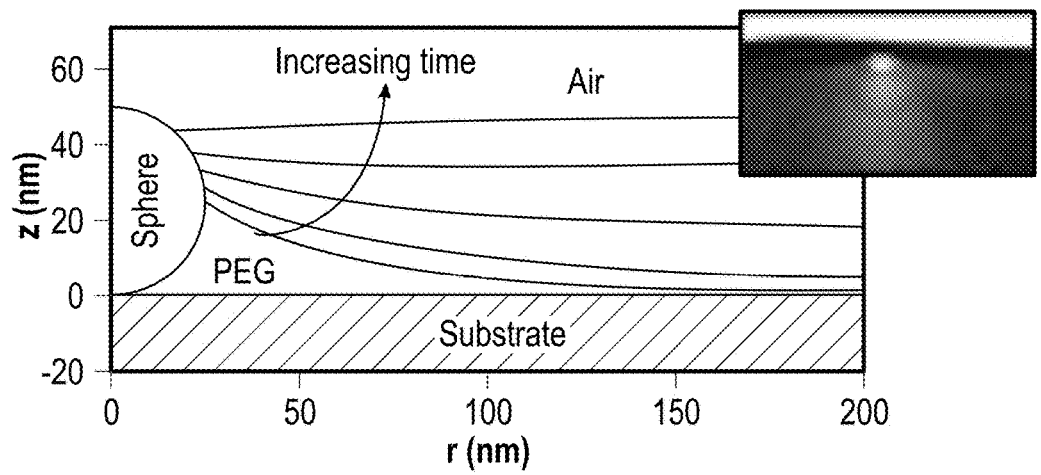
FIG. 3A illustrates a graphical illustration of how the nanolens surrounding a spherical nanoparticle thickens and changes shape over time. The inset shows a 3D rendering of the bead and nanolens.
Figure 3B:
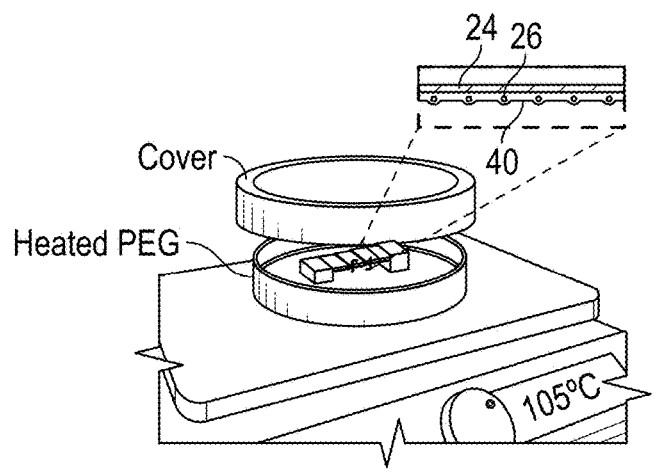
FIG. 3B illustrates an experimental apparatus used to generate vapor-condensed nanolenses of PEG. A substrate is suspended over a heated pool of liquid PEG in a closed chamber (dish with cover).
Figure 3C:
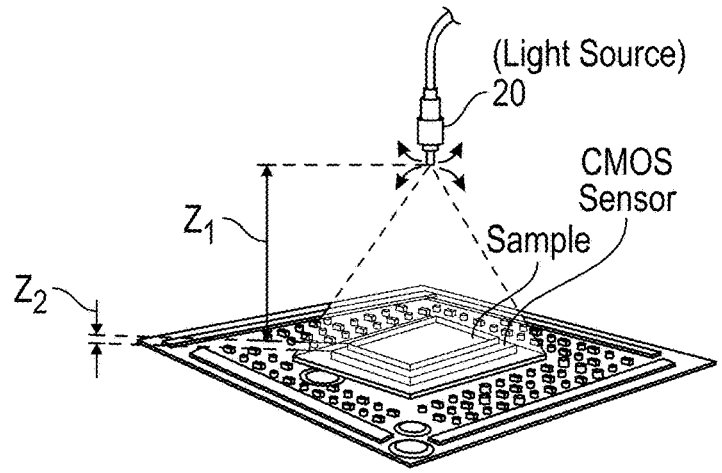
FIG. 3C illustrates a nanoparticle sample with vapor-condensed nanolenses being imaged using an ultra-wide field of view lens-free holographic on-chip microscope.
Figure 3D:
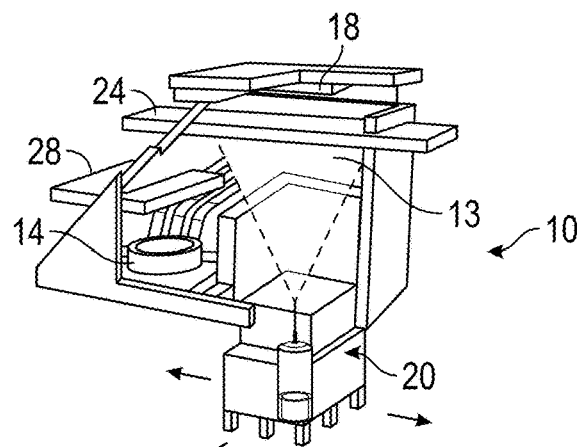
FIG. 3D illustrates a cut-way view of an embodiment of a field-portable or hand-held device for forming nanolenses and imaging particles.
Figure 3E:
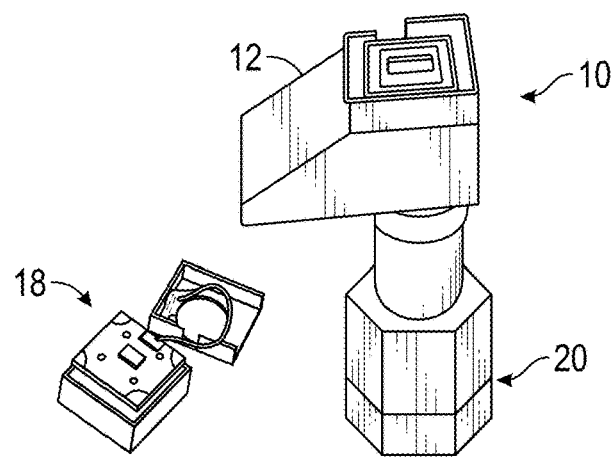
FIG. 3E is photographic image of a field-portable device according to one embodiment.

FIG. 3A illustrates how, as the liquid (in this example, PEG) condenses around a particle 26, the nanolens 40 surrounding particle 26 changes shape and thickens. The nanolens has an increased thickness as time progresses. FIG. 3B illustrates an experimental apparatus used to generate vapor-condensed nanolenses of PEG. A substrate is suspended over a heated pool of liquid PEG in a closed chamber (dish with cover). FIG. 3C illustrates an experimental setup used to obtained ultra-wide view, lens-free holographic microscope images of a substrate 24 containing the particles 26. In this experimental setup, the substrate 24 is inverted (after nanolens formation) with the particles 26 located on the upper surface to be imaged in the microscope setup of FIG. 3C. FIG. 3D illustrates an embodiment of a field portable device 10. FIG. 3E illustrates a photographic image of an embodiment of a field portable device 10.

In addition or as an alternative to obtaining actual images of the particles 26, the captured image data may be used to quantify the size and/or shape of the particles 26 located on the substrate 24. For example, the size of each particle 26 may be determined. A size distribution of all the particles 26 on the substrate 24 may also be calculated (this could also be a shape distribution). The image data may also be used to determine or calculate a density of particles 26 on the substrate 24. The density may include a density per area for two-dimensional particle deposition. In some embodiments, where there are a lot of particles 26 deposited, a three-dimensional for volume density may be calculated.

The captured image data may also be used to identify specific particles 26 that are deposited on the substrate 24. The identification of particles 26 may be made by the size or shape of the particles 26 according to one embodiment. In another, the spectral content or response of the particle 26 may be used to identify the nature of the particle(s) 26 of interest. In yet another alternative, the location of the particle 26 on the substrate 24 may also be used to identify the particle 26. For example, if a binding agent is used, the location of the binding agent is known in advanced and if a particle 26 is seen at a particular location on the substrate 24, this information can be used to identify the particle 26. The size, shape, spectral content, and location data may be contained in image processing software or a database that is used in connection with the computing device 32. For example, "finger print" like data that uses one or more parameters of size, shape, spectral content, and location may be stored and accessed to identify the type of particle 26.

In another alternative embodiment of the invention, the substrate 24 that is used for nanolens formation is chilled or cooled to a reduced temperature and then exposed to vapor (e.g., condensing vapor) that then condenses around particles 26 to form the lenses 40. For example, the substrate 24 could be chilled using a refrigerator, thermo-electric cooler, ice-bath, or the like that reduces the temperature of the substrate 24 below room temperature. The substrate 24 can then be exposed to a vapor that then condenses on the substrate 24 around the particles 26. The vapor may be, in one example, ambient humidity (e.g., water vapor) that exists naturally. Alternatively, a source of liquid may be provided in a reservoir 14, 52 that is located in an enclosed chamber or housing. This liquid may include water or a polymer fluid. The reservoir 14, 52 may, optionally, not be heated in this embodiment as vapor may naturally generate from the fluid in the reservoir 14, 52. Of course, it may also be heated in other embodiments.

EXPERIMENTAL

First, to deposit the nano-particles or nano-objects of interest on a hydrophilic plasma-treated glass coverslip, any one of a variety of methods can be used such as evaporation of a solvent, adsorption from a slowly flowing suspension, or specific biochemical linkage (e.g., binding agent). Next, the sample with adsorbed particles is suspended over a shallow pool of liquid polyethylene glycol (PEG) preheated to 105° C., as shown in FIG. 3B. The particles are exposed to PEG vapor for e.g., two minutes, during which a nanofilm of PEG condenses on the sample substrate. In the vicinity of the nanoparticles on the substrate, this film rises in the form of a meniscus, which forms a nanolens as seen in FIG. 3A.

To quantify the nanolenses' ability to enhance the scattering signals of the embedded nanoparticles, a pixel super-resolved lens-free holographic on-chip microscope was used as illustrated in FIG. 3C. This imaging modality provides a number of advantages over conventional microscopy, including cost-effectiveness (no expensive imaging optics), field-portable implementations (see e.g., FIGS. 1, 3D, and 3E), high resolution up to 0.9-1 effective numerical aperture, the ability to generate phase-contrast images, and an ultra-large field of view of >20 mm$^2$ (FIG. 4A) that is more than a thousand times larger than that obtained with a typical high-NA objective lens. In this lens-free on-chip imaging configuration (FIG. 3C), the transparent sample is placed in close proximity to the image sensor ($z_2$=50-300 µm), and is illuminated with a narrow-band light source emanating from an effective aperture size of ~100 µm. In this form of partially-coherent on-chip microscopy, the captured raw frames are in-line holograms of the specimen with unit magnification, which can be computationally reconstructed to form hi-fidelity phase and amplitude images of the sample with submicron resolution over the entire active area of the opto-electronic sensor-array. Note that in this embodiment x and y offsets can be accomplished by moving the light source (e.g., multimode optical fiber) in the x and y directions to obtain the sub-pixel shifts used to generate the super pixel-resolved holograms. Alternatively, the sample and/or image sensor could be moved in the x and y directions. As noted herein, for the portable embodiment illustrated in FIGS. 3D and 3E a diagonal array of LEDs can be used. Also, an array of LEDs in rows and columns could also be used (e.g., a 2D array).

Figure 4A:
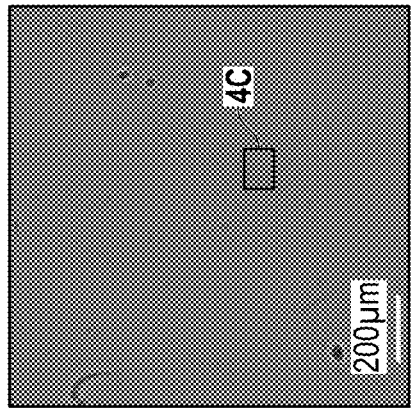
FIG. 4A illustrates a full field-of-view (FOV) of a holograph images of nano-objects (polystyrene (PS) nanoparticles) imaged with the aid of vapor-condensed nanolenses.
Figure 4B:
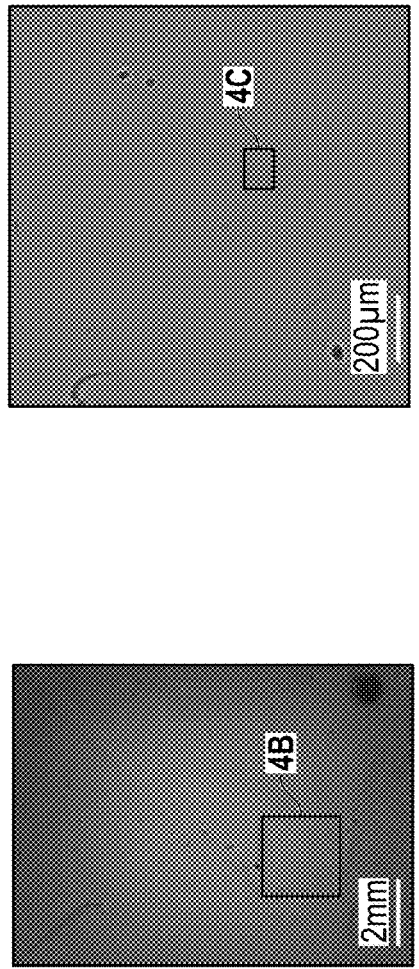
FIG. 4B illustrates a super-resolved, zoomed-in image of the highlighted square region of FIG. 4A.
Figure 4C:
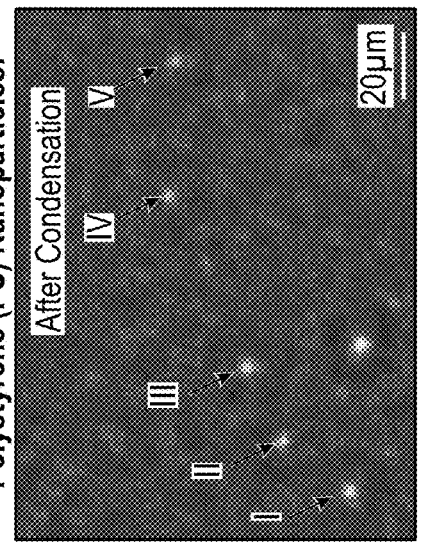
FIG. 4C illustrates a reconstructed phase image of a region of interest seen in FIG. 4B. No particles are visible because their respective holographic signals are too weak.
Figure 4D:
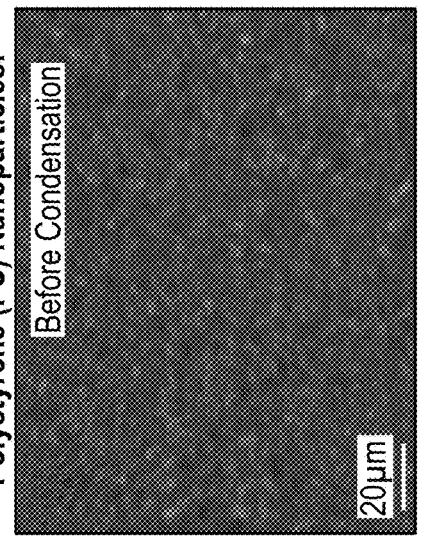
FIG. 4D illustrates reconstructed phase image of the region of interest after the condensation of nanolenses, individual particles in the same region of interest of FIG. 4C now become visible.
Figure 4F:
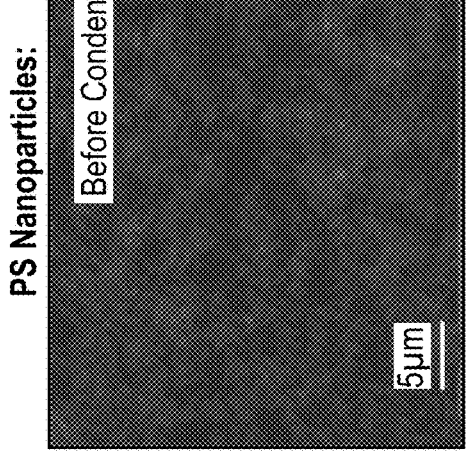
FIG. 4F illustrates another holographic image of a region of interest containing polystyrene (PS) nanoparticles before condensation.
Figure 4H:
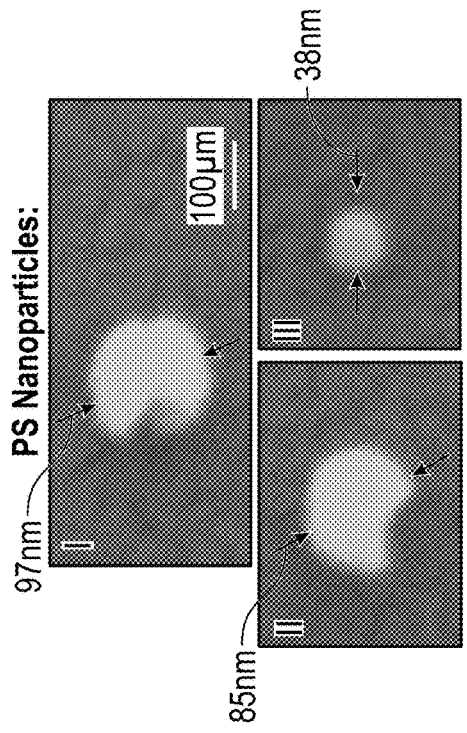
FIG. 4H illustrates SEM images of the particles of FIG. 4G. Measured dimensions are also illustrated.
Figure 4E:
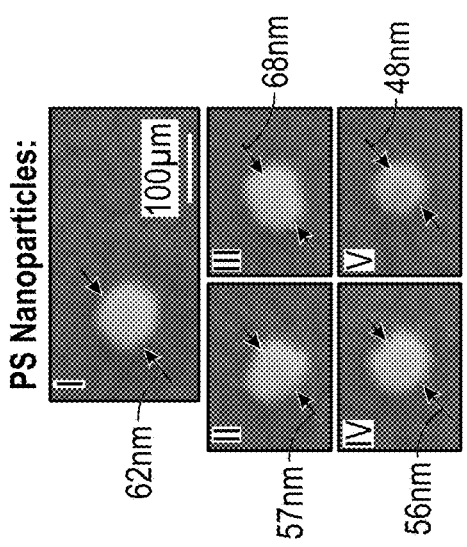
FIG. 4E illustrates SEM images that were used to verify the size of the particles that were detected in FIG. 4D.
Figure 4G:
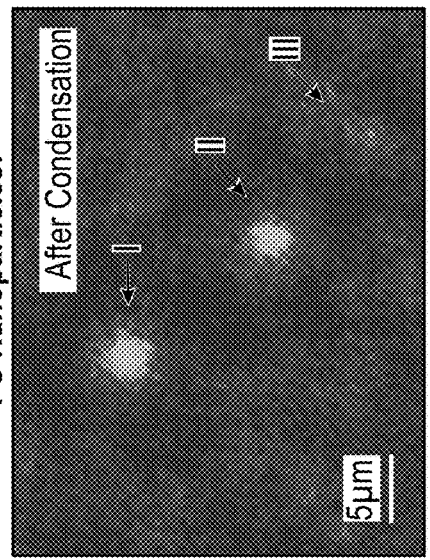
FIG. 4G illustrates another holographic image of a region of interest containing polystyrene (PS) nanoparticles after condensation. This region shows two larger, irregular particles, along with a particularly small, sub-40-nm particle.
Figure 4N:
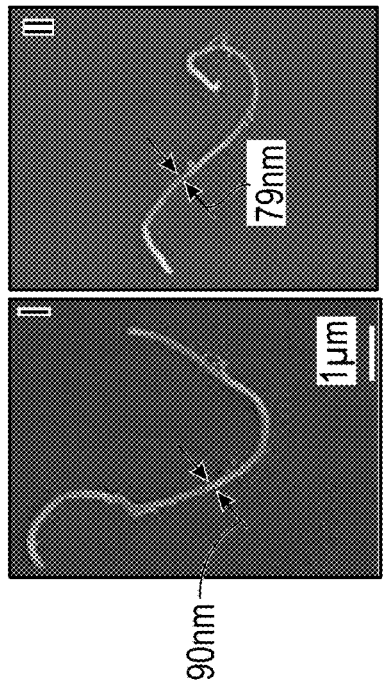
FIG. 4N illustrates SEM images of large CNTs of FIG. 4M. Measured dimensions are also illustrated.
Figure 4P:
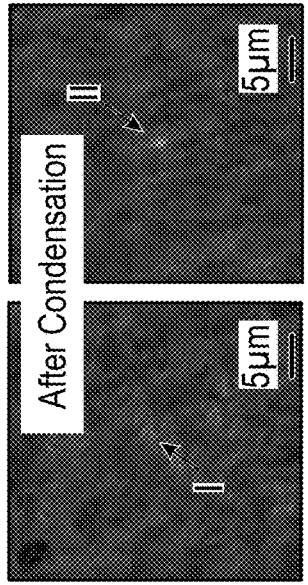
FIG. 4P illustrates another holographic image obtained after condensation of the region of interest containing smaller multi-walled carbon nanotubes. These tubes are too short for their shape to be correctly resolved, however they are still detectable.
Figure 4M:
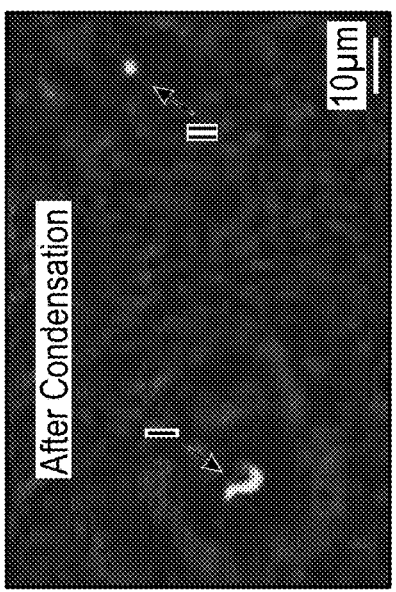
FIG. 4M illustrates another holographic image of the region of interest containing large, multi-walled carbon nanotubes (CNTs) after condensation, where the curved shapes of the nanotubes are visible.
Figure 4O:
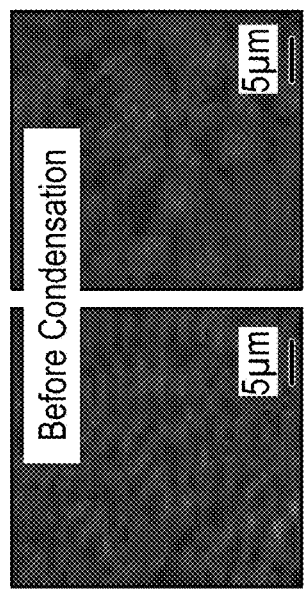
FIG. 4O illustrates another holographic image obtained before condensation of a region of interest containing smaller multi-walled carbon nanotubes (small CNTs) with diameters below 20 nm.
Figure 4Q:
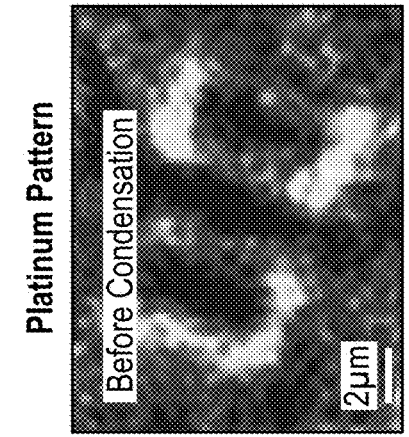
FIG. 4Q illustrates SEM images of the small CNTs. Measured dimensions are also illustrated.
Figure 4R:
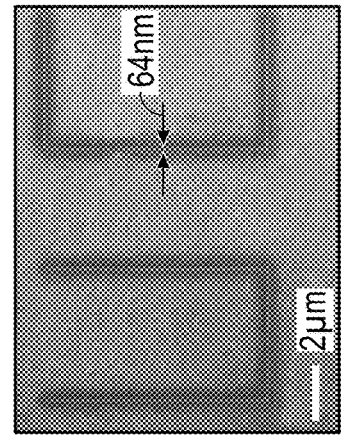
FIG. 4R illustrates a holographic image of a platinum pattern deposited on an indium-tin-oxide substrate using a focused electron beam prior to condensation.
Figure 4S:
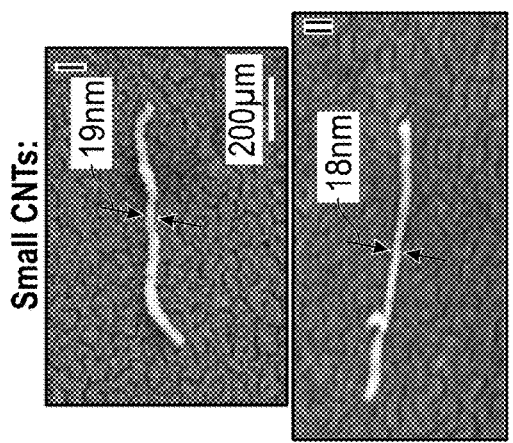
FIG. 4S illustrates the same region of FIG. 4R after condensation. Although parts of this pattern are still visible in the 'before' image in FIG. 4R, the contrast is significantly improved by condensation of nanolenses. For FIGS. 4F, 4G, 4I, 4J, 4L, 4M, 4O, 4P, 4R, and 4S, for each pair of 'before' and 'after' images, the same color map is used for both figures, although the working distance, $z_2$, may be slightly different.
Figure 4T:
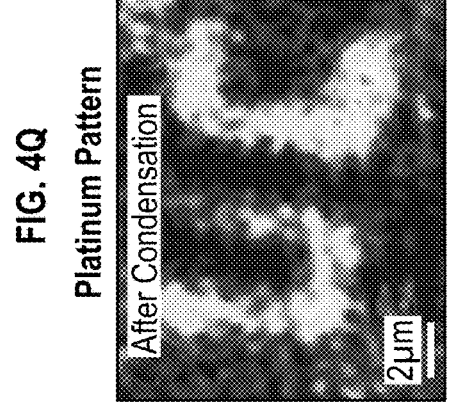
FIG. 4T illustrates a SEM image of the platinum pattern.

FIGS. 4A-4T, illustrate the results of a variety of different nano-objects whose imaging is enabled through the combination of vapor-deposited nanolenses and lens-free holographic on-chip microscopy. Types of particles include polystyrene beads (FIGS. 4A-4H), gold nanoparticles (FIGS. 4I-4K), carbon nanotubes (FIGS. 4L-4Q), and a platinum-based pattern written on an indium-tin-oxide substrate (FIGS. 4R-4T). For each set of nano-objects, control images of lens-free reconstructions of the sample without condensed nanolenses are shown along with lens-free reconstructions of the same regions of interest with condensed nanolenses. SEM images of the target particles for true size determination are also seen in FIGS. 4H, 4K, 4N, 4Q, and 4T. For lens-free images, reconstructed phase images were used, which provide the highest sensitivity and contrast for these small particles. Reconstructed phase images are obtained from the pixel super-resolution holographic image that is obtained from the plurality of lower resolution hologram images obtained using sub-pixel shifting in the x and y directions. The reconstructed image is obtained by retrieving the lost phase from the pixel super-resolution holographic image.

In addition to the ability to detect significantly smaller particles, this condensation-based approach to nanolens formation provides flexibility in terms of the particle surface chemistry. One example of this is the carbon nanotubes shown in FIGS. 4L-4N. These nanotubes are highly hydrophobic and incompatible with aqueous solutions. Here nanotubes were deposited on the substrate by first suspending them in acetone, and then letting the acetone evaporate. Despite the nanotubes' hydrophobic surface chemistry, PEG nanolenses provided commensurate enhancement as found for the more hydrophilic polystyrene beads.

Biochemically-functionalized particles can also be detected using vapor-condensed nanolenses after specific capture. This capability is particularly useful when trying to identify a specific type of particle from a heterogeneous solution (e.g. a virus or protein in whole blood or other body fluid). In FIGS. 5A-5J, a proof-of-concept approach is illustrated to image specific nanoparticles captured based on the interaction between biotin and streptavidin.

Figure 5A:
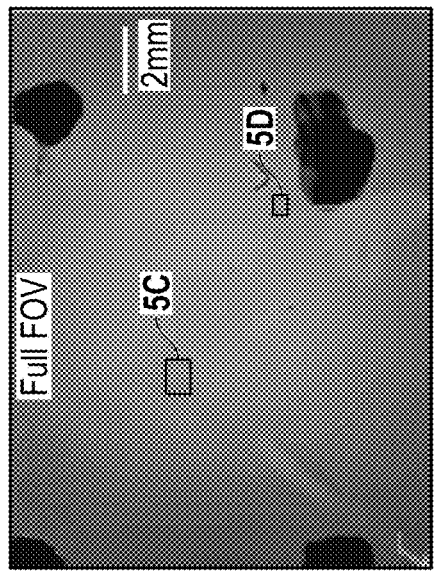
FIG. 5A illustrates a conventional 40× fluorescent microscope image of the bead mixture on a non-functionalized substrate. A large amount of 100 nm non-coated beads can be seen, as can a few streptavidin-coated 110 nm beads.
Figure 5B:
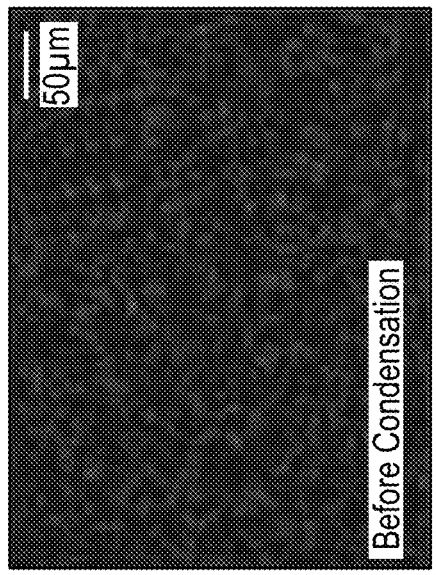
FIG. 5B illustrates a full FOV holographic on-chip image of streptavidin-coated beads (prior to condensation) specifically captured on biotinylated glass, mimicking the capture of virus-sized particles.
Figure 5C:
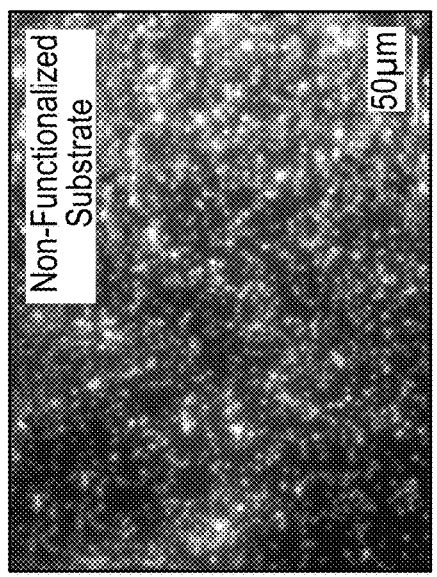
FIG. 5C illustrates a first region of interest before condensation showing that beads cannot be detected without condensed nanolenses.
Figure 5D:
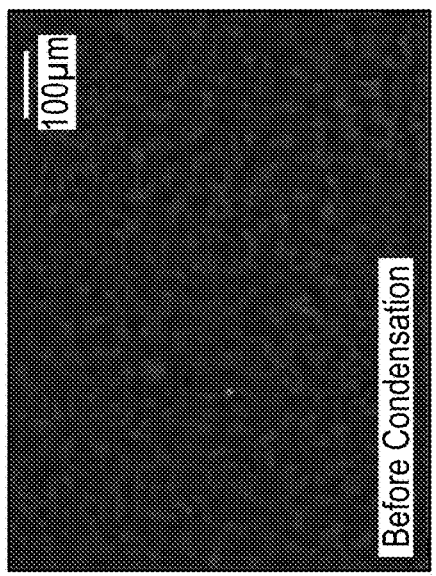
FIG. 5D illustrates a second region of interest before condensation again showing that beads cannot be detected without condensed nanolenses.
Figures 5I, 5J:
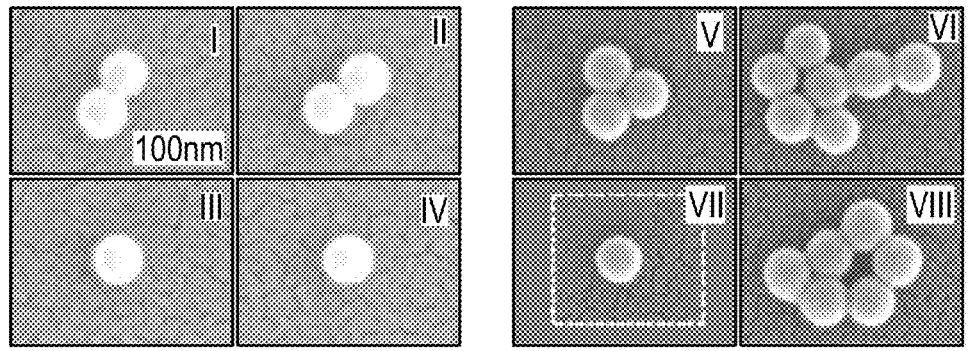
FIG. 5I illustrates SEM images that verify the sizes of the detected particle clusters from FIG. 5G.
FIG. 5J illustrates SEM images that verify the sizes of the detected particle clusters from FIG. 5H. For all lens free images, the working distance is $z_2 \approx 280$ μm.

In this experiment, an aqueous mixture of plain red fluorescent nanobeads and streptavidin-coated green fluorescent nanobeads were prepared, both ~100 nm. When a drop of this solution is deposited on a substrate and left to evaporate, one can measure the ratio of plain red beads to streptavidin green beads, which was 3.9:1 (FIG. 5A). To achieve specific capture of the green streptavidin-coated beads, a biotinylated glass slide was used as a substrate (see Methods below). This process provides excellent specificity with minimal non-specific binding, as verified using fluorescent microscopy in FIG. 5E and FIG. 5F, which show many green beads and no red beads. After using surface chemistry to provide specific capture of the desired nanobeads, holographic on-chip microscopy and vapor-condensed nanolenses were used to image the captured particles. As a control experiment, on-chip holographic imaging without nanolenses was used to attempt to detect the specifically captured beads (FIG. 5C and FIG. 5D). As expected, beads this small are undetectable in this lens-free on-chip imaging setup. After vapor-condensing nanolenses on the sample with a short plasma treatment to make the surface hydrophilic, the captured beads are now easily visible using on-chip holographic microscopy. The particle locations observed after nanolens deposition (FIGS. 5G and 5H) coincide with the particle locations measured using a conventional fluorescence microscope before plasma treatment and deposition (FIGS. 5E and 5F). SEM images are also used to verify the size and shape of the objects that were detected (FIGS. 5I and 5J).

Figure 6A:
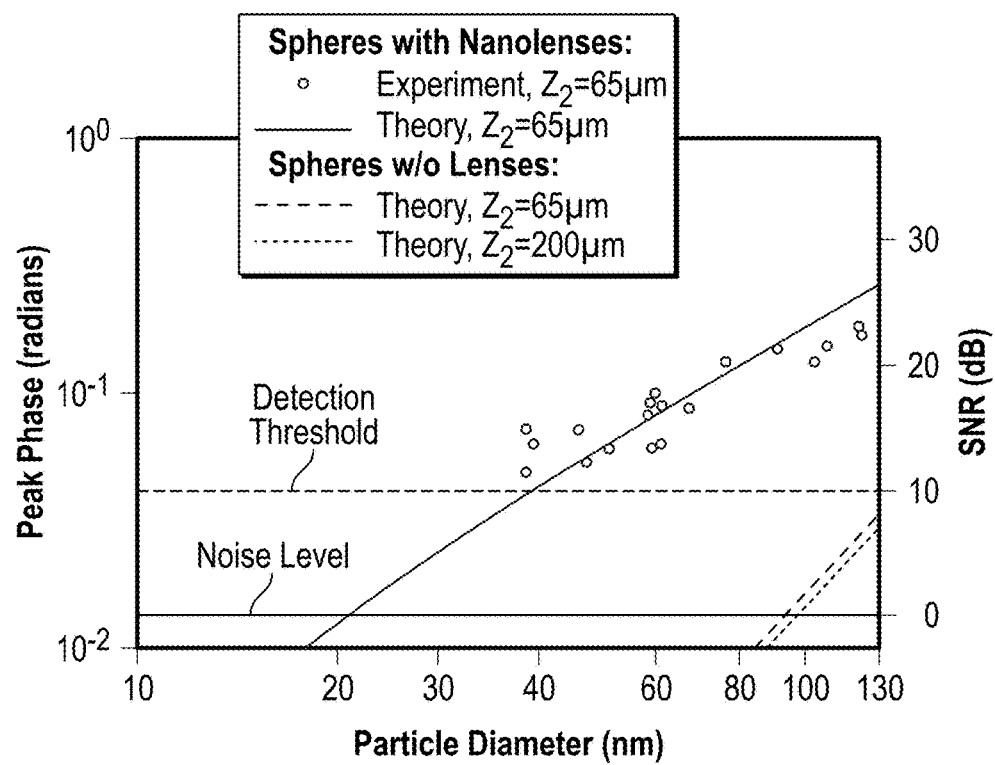
FIG. 6A illustrates experimental and simulated signal levels of sphere-shaped nanoparticles (spheroidal polystyrene particles) with and without vapor-condensed nanolenses. Vapor-condensed nanolenses raise the nanoparticle signal levels above the detection threshold. The solid line was determined using the vapor density as a fitting parameter, with value $3.6 \times 10^{15}$ molecules/m$^3$. The dashed lines used no fitting parameters. For 40 nm particles, there is ~50 fold improvement in signal level for particles with nanolenses compared to those without. The root-mean-square noise level was measured experimentally in several experiments, and found to be ~0.014 radians. The empirically-determined detection threshold is set at 3 times the background noise level, which also corresponds to what a human observer can reliably discern relative to background fluctuations.

To quantify the signal enhancement provided by vapor-condensed nanolenses, FIGS. 6A and 6A plot the peak reconstructed phase signal (i.e., greatest pixel value) from holographic on-chip images for both polystyrene spheroidal particles (e.g. those shown in FIGS. 4A-4H), and carbon nanotubes (e.g. those shown in FIGS. 4L-4Q). These plots show that phase signal scales with particle diameter, and that the threshold for particle detection using the nanolenses lies below 40 nm for spheres, and 20 nm for carbon nanotubes.

The performance of this platform can be further improved in terms of limit of detection by using e.g., a high bit-depth and cooled image sensor chip to further push the noise level down. The analysis reported in FIGS. 6A and 6B reveals that for objects with <50 nm feature size the vapor-condensed nanolenses improve the detection SNR by as much as 35 dB and 20 dB for spherical and rod shaped nano-particles, respectively.

To better understand how vapor-condensed nanolenses enhance the phase signal, and what kinds of nanolenses perform best, nanolens growth was modeled, along with their optical responses. These results were then compared to experimental measurements in FIGS. 6A and 6B. In modeling the nanolens growth, it was assumed that the condensation is film-wise, i.e. any PEG vapor molecule that hits the substrate will condense, and the driving force for condensation is sufficiently strong due to the undercooling of the substrate such that there is no nucleation barrier. Under the film-wise model, surface tension causes the film to rise in the form of a meniscus around embedded nanoparticles (FIG. 3A), thereby forming the signal-enhancing nanolens. As detailed in the Methods section herein, the shape of the nanolens can be calculated from the Young-Laplace equation with the inclusion of a van der Waals disjoining pressure, which can be significant for films this thin. The boundary conditions used for the Young-Laplace equation are the contact angle at the particle and the film thickness at large r. At the particle, a contact angle of 50° was assumed based on the macroscopically-measured contact angle of PEG on polystyrene, as well as measurements of PEG contact angles on carbon nanotubes, which have a similar value of 57.4°±5.9°. However, it is important to note that especially for the polystyrene beads used, the particle contact angle has not been well-characterized in our nanoscale system, and effects resulting from surface chemistry of the particle, surface roughness, and van der Waals interactions could alter the contact angle. Fortunately, simulations show that the results of this model are not especially sensitive to moderate variations in contact angle. The second boundary condition, the film thickness far away from nanoparticles, is determined by the time and temperature of the condensation process. It grows linearly in time at a rate determined by the vapor density. With the governing equation and boundary conditions established, the lens shapes can be calculated as a function of time for both spherical particles (e.g., FIG. 3a) and rod-shaped particles.

The optical properties of the nanoparticles and lenses are modeled using a thin-lens approximation with a laterally-varying vertically-integrated optical path length determined by the nanoparticle and lens topography. In a previous study, we have compared this type of model to a finite-difference time-domain model, and found the two models to be equivalent. Based on this thin-lens approximation, the in-line hologram formed by the object using the angular spectrum approach is computed, which simulates the complex optical field at the complimentary metal-oxide-semiconductor (CMOS) image sensor plane. As the CMOS image sensor can only sense the intensity of the hologram, only the amplitude information from the field at this plane is kept, down-sample it to a super-resolved pixel size of 0.28 μm, and then back-propagate to the object plane, again using the angular spectrum approach. This simulation thus replicates the way the experimental data is processed to retrieve phase and amplitude images of specimen. After back-propagation, the peak value of the phase for different particle diameters is recorded and this data is plotted as lines in FIGS. 6A and 6B.

In performing these simulations, a single fitting parameter was used: the effective PEG vapor density, which depends on the PEG heating temperature. This parameter was chosen to provide the best fit between experiment and theory for spheres with nanolenses in FIG. 6A. This fitting parameter was necessary to accurately simulate the non-equilibrium condensation with the steady-state model. In the experiment, it is difficult to quantify the true PEG vapor density due to the short duration of the experiment and initial transient fluctuations from mixing with ambient air during sample insertion. However, we would expect the true PEG vapor density to lie somewhere between the saturated vapor densities at room temperature (25° C.) and at the heated PEG reservoir temperature of 105° C. Indeed, the best-fit PEG vapor density of $3.6 \times 10^{15}$ molecules/m$^3$ corresponds to the saturated vapor density at 40° C., and thus falls within the expected bounds.

Figure 6B:
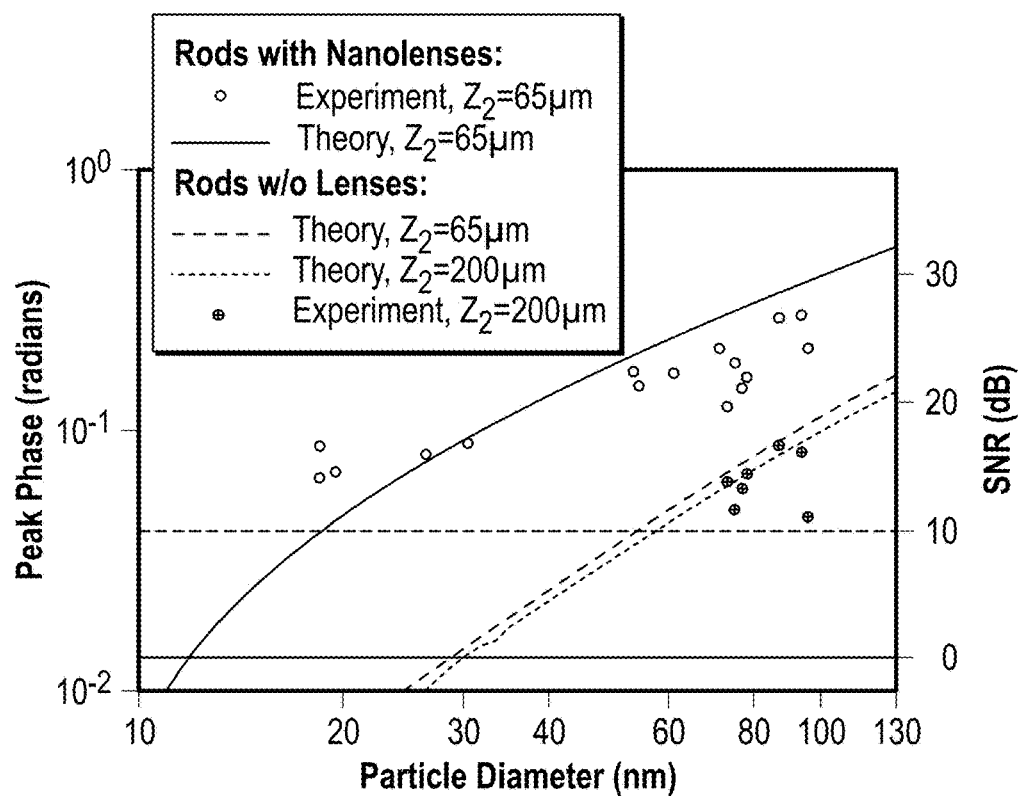
FIG. 6B illustrates experimental and simulated signal levels of rod-shaped nanoparticles (Rod-shaped carbon nanotubes) with and without vapor-condensed nanolenses. The minimum detectible diameter (D) is smaller for rod-shaped particles than for spheroidal particles. The larger carbon nanotubes are experimentally detectable without nanolenses. Their signal values agree well with theoretical predictions. No fitting parameters were used in this panel; the solid line uses the same vapor density as in FIG. 6A.

Further validation of the theoretical model is obtained by testing its predictions for carbon nanotubes using the same value of the effective PEG vapor density, shown in FIG. 6B. These results, along with the results of the control simulations (nanotubes without nanolenses, dashed lines in FIG. 6B), which used no fitting parameters, show continued good match between experiment and simulation. Note that spheroidal particles do not provide a strong enough signal to be measured without nanolenses, and thus cannot be directly compared with simulation predictions. Although it does not significantly affect the recovered signal, the control simulations of particles without nanolenses were conducted at two different working distances to match experimental conditions.

Interestingly, the addition of nanolenses changes the characteristic scaling of the phase signal $\phi$ with respect to particle diameter, reducing its exponent (q, where $\phi \sim D^q$), as evident from the reduction in slope shown on the log-log plots in FIGS. 6A and 6B upon deposition of nanolenses. A reduction in exponent corresponds to enhanced signals from smaller particles. Rayleigh scattering theory predicts a scattered power from nanoparticles $P \propto D^6$, which would apply to microscopy modalities such as dark-field microscopy. In contrast, holographic microscopy records the interference of the scattered wave with a reference wave, with a signal that is proportional to scattered field amplitude, reducing the scaling exponent from q=6 to q=3. Note that the simulations for spherical particles without nanolenses shown in FIG. 6A show consistent scaling with q=3.0 for $z_2$=200 μm, and q=2.9 for $z_2$=65 μm. After the deposition of vapor-condensed nanolenses, the exponent reduces even further to q=1.6, based on a linear fit to the solid blue curve for 100 nm<D<130 nm. For rod-shaped particles, the exponents do not initially follow Rayleigh scattering theory (q=2) because the rods are simulated with a complex refractive index (absorption) and with a length significantly longer than the wavelength of light, where Rayleigh theory fails. The rod simulation exponents, again for 100 nm<D<130 nm, are q=1.5 for $z_2$=65 μm without nanolenses, q=1.4 for $z_2$=200 μm without nanolenses, and q=1.1 for $z_2$=65 μm with nanolenses. Therefore, one can conclude that vapor-condensed nanolenses reduce the scaling exponent for rod-shaped particles, just as they did with spherical particles. This reduction in scaling exponent is commensurate with significantly improved signal.

The effect of condensation time and PEG vapor density on recovered phase signal was investigated with the results illustrated in FIG. 7, which provide two modes of tunability to improve the detection performance by >30 dB for the 50 nm spherical particles simulated here. For a given vapor density, the phase signal shows an optimum in time because small levels of condensation only generate small lenses, while very large amounts of condensation end up burying a particle under a thick continuous film, entirely eliminating the lensing effect. As one might expect, greater vapor densities produced from higher PEG heating temperatures speed up the lens growth rates. For comparison to previous work, we also show the phase signal that is theoretically predicted for a catenoid-shaped minimal-surface nanolens of the type formed through a previous liquid flow-method of producing nanolenses. We see that such a non-tunable minimal-surface based nanolens would not boost the phase signal above the detection threshold for e.g., D=50 nm, and that the tunability afforded by vapor-condensed nanolenses provides significant detection advantages.

In summary, a method to fabricate tunable self-assembled nanolenses around nanoparticles using the condensation of PEG from the vapor phase has been demonstrated. These nanolenses have been used to significantly boost SNR for the detection and localization of nanoparticles across an ultra large field of view using lens-free holographic on-chip microscopy. These vapor-condensed PEG nanolenses perform significantly better than previous non-tunable nanolenses, enabling the detection of spherical particles below 40 nm, and rod-shaped particles with diameters below 20 nm. The optical enhancement provided by these nanolenses agrees very well with theory. This vapor-based condensation approach also provides the advantages of compatibility with various surface chemistries and compatibility with specific and sensitive particle capture based approaches necessary for isolating bio-nanoparticles from multi-component samples. Furthermore, both the nanolens vapor condensation and its wide-field on-chip imaging can be performed within a cost-effective and portable device of the type illustrated in FIGS. 1, 3D, 3E, which may find wide-scale use in field settings as well as mobile sensing and diagnostics applications. These developments can pave the way for label-free and field-portable detection of biological nanoparticles such as viruses in complex heterogeneous samples including e.g., whole blood and other bodily fluids. In a broader context, this method of constructing tunable nanolenses centered on protrusions in a substrate may prove useful for fabricating lithographically-controlled nanolenses for other nano-imaging and detection applications.

Methods

Sample Preparation.

For deposition of nanoparticles on the substrate, a #1 cover glass was used and depends on the type of nanoparticles. For polystyrene beads (FIGS. 4A-4H, FIG. 6A), manufacturer stock solutions (Invitrogen F8800, F20886, F8783) are diluted between 5 million-fold and 500 million-fold in alcohol (either ethanol or isopropanol), and a 1-5 μL drop is deposited on a plasma-treated (Electro-Technic Products, BD-10AS) cover glass, and left for the solvent to evaporate. For gold nanoparticles (FIGS. 4I-4K), manufacturer stock solutions (nanoComposix, DAC1278) are diluted several hundred times in a Tris/PEG-600/HCl mixture (Sigma-Aldrich, 07066), a 6 μL drop of which is deposited on a plasma-treated cover glass and left to sediment for 5 minutes, after which the excess liquid is removed by tilting the substrate. This procedure forms minimal-surface nanolenses, which are further improved by the vapor-condensed nanolenses added later. For multi-walled carbon nanotubes (FIGS. 4L-4Q and FIG. 6B), the as-received powder (CheapTubes, 03040203, 03040204, 030104, 030106, 030107) is suspended in acetone at concentrations between 0.1 μg/mL and 1 mg/mL, and is deposited on a plasma-treated cover glass and left to evaporate. For the platinum direct-write pattern (FIGS. 4R-4T), the substrate is an indium-tin-oxide-coated glass 0.5 mm thick. A focused ion beam/scanning electron microscope system (FEI Nova 600 NanoLab) is used to locally deposit platinum on the substrate where the scanning electron beam is focused. The height-to-width aspect ratio of these patterns is approximately 1:1, and the line cross-sections are approximately Gaussian.

For the specificity experiments (FIGS. 5A-5H), the sample preparation was more specialized. First, a cover slip is biotinylated using the following procedure: (1) dissolve biotin-PEG-silane (Laysan Bio, Biotin-PEG-SIL-3400-1g) at a concentration of 6.8 mg/mL in 95% ethanol, 5% water, (2) plasma-treat using hand-held plasma treatment device (Electro-Technic Products, BD-10AS), (3) drop 10 μL of biotin solution onto cover glass, (4) wait for cover glass to dry, then rinse with deionized (DI) water. The bead mixture was prepared by combining 1 μL of the manufacturer stock solution of 110 nm green fluorescent streptavidin-coated beads (Bangs Labs, CP01F) and 0.4 μL of the manufacturer stock solution of 100 nm red fluorescent carboxylate-coated beads (Invitrogen, F8800) in 1 mL of water with 3% sodium dodecyl sulfate (SDS). This solution was diluted by a factor of 1:9 in water and 3% SDS, while in other experiments many different dilution factors were used. A 0.5 μL droplet of the solution was placed on the biotinylated cover glass, and an untreated cover glass was placed on top with 40 μm spacers between the two glasses. The sample was left for three minutes, and then disassembled, and the biotinylated cover glass was washed with DI water. The sample was imaged using fluorescence and lens-free imaging to acquire 'before' images. Finally, before condensing nanolenses, the back side of the sample was plasma treated to make the sample more hydrophilic.

Vapor Condensation.

Polyethylene glycol (PEG) 300 (Sigma-Aldrich, 202371) was poured into a 4-inch glass petri dish (FIG. 3B) to form a pool of liquid 2 mm deep. This petri dish was heated on a hot plate at 105° C. (110° C. in the case of FIGS. 4I-4K) for 30 min to allow for the evaporation of water and any particularly short PEG chains that happened to be present in the PEG 300. The nanoparticle sample was mounted upside-down on a bridge-shaped structure using double-sided tape such that the gap between the liquid pool of PEG and the sample was 4 mm (see FIG. 3B). The chamber was covered and left for 2 minutes, and then the sample was removed.

Holographic on-Chip Imaging.

A lens-free holographic on-chip microscope was used to image samples (FIG. 3C). This imaging platform has been described extensively in previous publications. The microscope includes automated source-shifting to capture pixel-super-resolved in-line holograms, resulting in a spatial resolution below 0.3 μm even under unit magnification, where the sample field of view equals to the active area of the CMOS imager. Images were obtained using 480 nm light with a bandwidth of 3 nm generated using a monochromator (Newport, 74100), projected from the end of a 100 μm core diameter fiber. The distance between the light source and the sample is $z_1$=6 cm. The working distance between the sample and the sensor (Sony, 16 megapixel, 1.12 μm pixel pitch) varied among the experiments: for FIGS. 4C, 4F, 4I, 4J, 4L, and 4O, $z_2$ was between 197 μm and 212 μm; for FIGS. 4D, 4G, 4M, 4P, 4R, and 4S $z_2$ was between 61 μm and 66 μm; for FIGS. 5A-5H, all lens-free images were acquired with $z_2$ between 280 μm and 290 μm; and for FIGS. 6A and 6B, all of the experimental data points after nanolens condensation were acquired with $z_2$ between 61 μm and 71 μm, while all of the experimental data points before nanolens condensation were acquired with $z_2$ between 181 μm and 198 μm. Raw low-resolution holograms were melded into a super-resolved hologram using a pixel super-resolution procedure described previously. These holograms are digitally reconstructed using the angular spectrum method, with the phase channel being used to report results. Noise levels were computed by finding the standard deviation of the background fluctuations in a region without particles.

Scanning Electron Microscopy for Independent Size Quantification.

Samples were coated with 13.6 nm of gold (8.5 nm of AuPD alloy in the case of FIG. 4K) using an ion beam sputterer, and imaged on a scanning electron microscope (FEI Nova 600 NanoLab). These coating thicknesses were calculated by observing the apparent change in size of nanoparticles as a function of coating time in the ion beam sputterer. When reporting SEM-measured particle sizes herein, these coating thicknesses were subtracted from the raw measurement of the thickness.

Lens Shape Modeling.

In the following analysis, effective vapor density, $n_0$, variable was used as a fitting parameter in comparing with experimental data. The molecular flux in the vapor can be derived from the Maxwell-Boltzmann distribution, and is given by the following equation:

$$J = \sqrt{\frac{kT_{sat}(n_0)}{2\pi m_1}} n_0,$$

where k is Boltzmann's constant, $m_1$=4.69×10$^{-25}$ kg is the mass of a single PEG molecule (assumed to have 6 monomer units so that the molecular weight ~300 Daltons). The temperature was chosen to be that of a saturated vapor with density $n_0$ at ambient pressure. Based on the ideal gas law:

$$T_{sat}(n_0) = \frac{p_{vap}}{kn_0},$$

where $p_{vap}$ is the partial pressure of the saturated vapor, which is also a function of temperature. Using the curves for the vapor pressure of ethylene glycol, diethylene glycol, triethylene glycol, and tetraethylene glycol, the vapor pressure of PEG was extrapolated to be:

$$p_{vap} = 10^{-2.61\,M-5.03}(T_{sat}^{Cel})^{0.884\,M+4.61},$$

where M=6 is the number of monomers, and $T_{sat}^{Cel}$ is the saturation temperature in Celsius. These two equations can be solved numerically to find $T_{sat}(n_0)$, which is expected to lie somewhere between room temperature, and the heated PEG temperature (typically 105° C.). Under the assumption of film-wise condensation, there is no nucleation barrier to condensation on the substrate, and therefore the condensing film thickness is given by:

$$h_0(n_0,t) = JV_1 t,$$

where $V_1 = m_1/\rho_{PEG}$ is the volume of a single molecule of PEG ($\rho_{PEG}$=1130 kg/m$^3$)[58], and t is time.

The shape of the nanolens (meniscus) that forms around an embedded particle is found by solving the Young-Laplace equation with a disjoining pressure:

$$\Delta p = \rho_{PEG} g h(r) - 2\gamma K_m(r,h(r)) + \Pi(h(r)),$$

where Δp is the pressure drop across the liquid-vapor interface, g is acceleration due to gravity, h is the local height of the interface, γ=42.2 mN/m is the surface tension of the PEG at 40° C., $K_m$ is the local mean curvature of the interface, and Π(h) is the disjoining pressure of the film due to van der Waals interactions, given by:

$$\Pi(h) = -\frac{A_{123}}{6\pi h^3},$$

where $A_{123}=-6.3\times10^{-21}$ J is the Hamaker constant for a glass-PEG-air system. As Δp is space-invariant, one can compute it far from the nanoparticle, where the film is essentially flat ($K_m$=0):

$$\Delta p = \rho_{PEG} g h_0 - \frac{A_{123}}{6\pi h_0^3}.$$

In a cylindrical coordinate system, which applies to modeling the lens formed around spherical nanoparticles, the mean curvature can be derived from a cylindrical parameterization of the surface, and expressed in either of the two forms:

$$2K_m = \pm\left(\frac{\frac{dh}{dr}}{r\sqrt{1+\left(\frac{dh}{dr}\right)^2}} + \frac{\frac{d^2h}{dr^2}}{\left(1+\left(\frac{dh}{dr}\right)^2\right)^{3/2}}\right),$$

$$2K_m = \pm\left(\frac{1}{r\sqrt{1+\left(\frac{dr}{dh}\right)^2}} - \frac{\frac{d^2r}{dh^2}}{\left(1+\left(\frac{dr}{dh}\right)^2\right)^{3/2}}\right).$$

The analytical form which is most convenient depends on the local slope and curvature of the interface (i.e., whether is h a single-valued function of r, or is r a single-valued function of h). After substituting these expressions into the Young-Laplace equation, it can be seen that the Young-Laplace equation is a second-order nonlinear ordinary differential equation (ODE), and thus requires two boundary conditions. The film thickness at infinity, $h_0$, is one boundary condition, and the contact angle of the film at the particle $\theta_p$, is the other boundary condition.

One can numerically solve this nonlinear ODE using a custom-written MATLAB program that sequentially solves a number of initial value problems that trace the interface starting from the particle and moving outward. These initial value problems are characterized by the initial slope of the interface based on the assumed $\theta_p$ and the contact height of the interface at the particle (0≤$h_p$≤D), where D is the particle diameter. As this interface is traced outward from the particle, the solver intelligently switches between the two forms of the mean curvature, and so can handle interfaces that completely curve back on themselves. This approach automatically satisfies the boundary condition given by $\theta_p$, while the boundary condition of the film thickness at infinity being $h_0$ is satisfied by selecting the film shape corresponding to the initial contact height $h_p$ that results in h→$h_0$ as r→∞. These results are shown in FIG. 3A for the time-varying $h_0$.

For modeling the lens shape around rod-shaped particles, the approach is similar. Here one assumes that the rod is oriented along the x-direction such that the meniscus falls away from the rod in the y-direction. Then, the Young-Laplace equation becomes, $$\Delta p = \rho_{PEG} g h(y) - 2\gamma K_m(y,h(y)) + \Pi(h(y)),$$

and the two mean curvature expressions are:

$$2K_m = \pm\frac{\frac{d^2h}{dy^2}}{\left(1+\left(\frac{dh}{dy}\right)^2\right)^{3/2}},$$

$$2K_m = \pm\frac{\frac{d^2y}{dh^2}}{\left(1+\left(\frac{dy}{dh}\right)^2\right)^{3/2}}.$$

The rods were generally modelled as being 5 μm long; rods between 500 nm and 10 μm long show approximately constant signal with variations less than ±15%. For the rod end caps hemispheres were used with lens shapes predicted by the spherical particle solution. This approximation in lens shape at the edge does not reflect the true lens shape at the edges, which would require a more advanced finite-element approach to model. However, these errors in edge-effects should only have a minor contribution to the recovered phase signal compared to the long body of the rod being simulated. The remaining steps in modeling lenses around rod-shaped particles are the same as for modeling lenses around spherical particles.

Optical Modeling.

Figure 7:
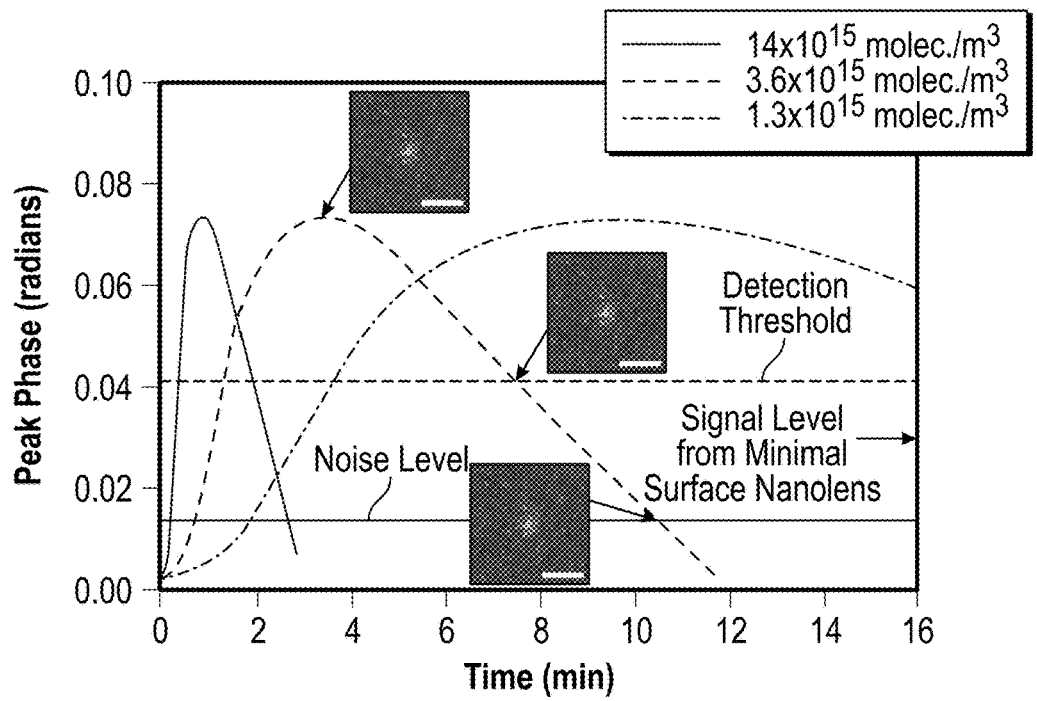
FIG. 7 illustrates tunability of signal enhancement based on time and vapor density. The level of the phase signal for 50 nm beads is simulated for three different vapor densities, corresponding to different heating temperatures. The three insets show the simulated reconstruction images with signal levels at the maximum, at the detection threshold, and at the noise level. Scale bars 5 μm. The noise level and detection threshold are based on experimental measurements (see FIGS. 6A/6B). The minimal surface nanolens phase (0.030 rad) is the result of a simulation of a catenoid-shaped nanolens with substrate contact angle of 2.5°.

To numerically model the holographic microscopic imaging of the nanoparticles and nanolenses, the nanoparticles and nanolenses were treated using the thin-lens approximation, which has been shown to be equivalent to an FDTD simulation for similar objects, although here the materials were modeled using complex refractive indices to account for absorption and scattering. For polystyrene particles, n=1.61 was used; for multi-walled carbon nanotubes, the refractive index of amorphous carbon, n=1.80+0.692 i was used; for PEG 300, n=1.46 was used. Using the above model for the lens shapes, the net optical path length (particle and lens together) was computed through each (x, y) point of the system, on a grid with interval size 3.5 nm and full dimensions of 83 μm×83 μm. Using the angular spectrum method, the hologram that is generated a distance $z_2$ away is computed when this material system is illuminated with a plane wave, which represents the hologram at the sensor plane. This hologram is then down-sampled to a super resolved pixel-size of 1.12 μm/4=0.28 μm, and its phase is set to zero, simulating the hologram that would be recorded experimentally. The resulting hologram is interpolated by a factor of 2, and then back-propagated, again using the angular-spectrum approach, which is the same procedure used to recover images experimentally. In these recovered images, the peak value of the phase image is recorded, which is seen plotted in FIGS. 6A, 6B, and 7.

What is claimed is:
1. A method of forming nanolenses for imaging comprising:
providing an optically transparent substrate having a plurality of particles disposed on one side thereof;

locating the optically transparent substrate within a chamber containing therein a reservoir holding a liquid solution;

heating the liquid solution to form a vapor within the chamber, wherein the vapor condenses on the substrate to form nanolenses around the plurality of particles; and illuminating the plurality of particles disposed on the substrate and capturing one or more images of the plurality of particles with an image sensor disposed adjacent to the substrate.

2. The method of claim 1, wherein the liquid comprises polyethylene glycol (PEG).

3. The method of claim 1, wherein the liquid solution is heated to a temperature within the range of 50° C.-250° C.

4. The method of claim 1, further comprising subjecting the one or more images to image processing to determine one or more parameters including particle location, particle size, particle shape, particle density, and spectral content.

5. The method of claim 4, further comprising identifying a particle based on the one or more parameters.

6. The method of claim 1, wherein the plurality of particles are exposed to the vapor for a period of time between several seconds and several minutes prior to capturing one or more images.

7. A method of forming nanolenses for imaging comprising:

providing an optically transparent substrate having a plurality of particles disposed on one side thereof;

locating the optically transparent substrate within a chamber containing therein a reservoir holding a liquid solution;

heating the liquid solution to form a vapor within the chamber, wherein the vapor condenses on the substrate to form nanolenses around the plurality of particles; and transferring the optically transparent substrate to an imaging device and capturing one or more images of the plurality of particles.

8. The method of claim 7, further comprising subjecting the one or more images to image processing to determine one or more parameters including particle location, particle size, particle shape, particle density, and spectral content.

9. The method of claim 8, further comprising identifying a particle based on the one or more parameters.

10. The method of claim 7, wherein the plurality of particles are exposed to the vapor for a period of time between several seconds and several minutes prior to transferring the optically transparent substrate.

11. A method of imaging particles comprising:

providing a closed housing or chamber that contains a liquid holding reservoir;

providing an optically transparent substrate having the particles disposed on one side thereof inside the closed housing or chamber;

heating a liquid solution contained in the reservoir to generate vapor that is exposed to the optically transparent substrate, wherein the vapor condenses on the substrate to form nanolenses around the particles; and illuminating the plurality of particles disposed on the substrate and capturing one or more images of the plurality of particles with an image sensor disposed adjacent to the substrate.

12. The method of claim 11, wherein the liquid comprises polyethylene glycol (PEG).

13. The method of claim 11, wherein the liquid is heated to a temperature within the range of 50° C.-250° C.

14. The method of claim 11, wherein the particles comprise airborne particles.

15. The method of claim 11, wherein the particles comprise waterborne particles.

16. The method of claim 11, wherein the particles comprises biological particles.

17. A method of forming nanolenses for imaging comprising:

providing a chilled, optically transparent substrate having a plurality of particles disposed on one side thereof;

exposing the chilled substrate to a condensing vapor, wherein the vapor condenses on the chilled substrate to form self-assembled nanolenses around the plurality of particles; and illuminating the plurality of particles disposed on the substrate and capturing one or more images of the plurality of particles with an image sensor disposed adjacent to the substrate.

* * * * *